United States Patent [19]  [11] Patent Number: 4,536,314
Hardy et al.  [45] Date of Patent: * Aug. 20, 1985

[54] BLEACH COMPOSITIONS COMPRISING NON-LINEAR ALIPHATIC PEROXYCARBOXYLIC ACID PRECURSORS

[75] Inventors: Frederick E. Hardy, Newcastle upon Tyne, England; David J. Kitko, West Chester; Cushman M. Cambre, Cincinnati, both of Ohio

[73] Assignee: The Procter & Gamble Company, Cincinnati, Ohio

[ * ] Notice: The portion of the term of this patent subsequent to Nov. 1, 2000 has been disclaimed.

[21] Appl. No.: 582,421

[22] Filed: Feb. 22, 1984

[30] Foreign Application Priority Data

Feb. 23, 1983 [GB] United Kingdom ............... 8304990

[51] Int. Cl.³ .................. C11D 7/38; C11D 7/54; B32B 27/34
[52] U.S. Cl. ........................ 252/102; 252/90; 252/95; 252/99; 252/186.26; 252/186.38; 252/186.41; 260/402; 260/404; 260/404.5; 260/456 A; 260/513 N; 560/105; 560/130; 560/142; 560/157; 562/575; 564/152; 564/157; 564/159; 428/284; 428/289
[58] Field of Search .................. 252/90, 95, 99, 102, 252/186.38, 186.26, 186.41; 260/402, 404, 456 A, 513 N, 404.5; 560/142, 130, 105, 157; 562/575; 564/152, 157, 159; 428/289, 284

[56] References Cited

U.S. PATENT DOCUMENTS 4,248,928  2/1981  Spadini et al. ............... 428/286
4,348,293  9/1982  Clarke et al. ............... 252/90
4,374,747  2/1983  Tai ........................ 252/186.26
4,391,723  7/1983  Bacon et al. ............... 252/90

4,412,934  11/1983  Chung et al. ............... 252/186.38

Primary Examiner—Prince E. Willis
Attorney, Agent, or Firm—Robert B. Aylor; Richard C. Witte; Thomas H. O'Flaherty

[57] ABSTRACT

Detergent compositions, detergent additive products and bleaching compositions containing aliphatic peroxyacid bleach precursors of formula

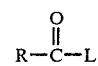

are provided, where L is a leaving group of defined formula whose conjugate acid has a pKa of from 6 to 13 and

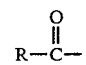

is a non linear acyl group, the carboxylic acid derivative of which has a $\log P_{OCT}$ in the range from 1.9 to 4.0 (where $P_{OCT}$ is the partition coefficient between octanol and water). New precursor compounds are provided in which

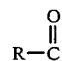

is a $C_7$–$C_{17}$ branched aliphatic acyl group containing a linear chain of at least 5 carbon atoms extending from and including the carbonyl carbon wherein the branching is on at least the 2- and/or 3- carbon atom.

39 Claims, No Drawings

BLEACH COMPOSITIONS COMPRISING NON-LINEAR ALIPHATIC PEROXYCARBOXYLIC ACID PRECURSORS

FIELD OF THE INVENTION

This invention relates to the field of oxidisable stain removal, especially but not solely to the removal of oxidisable stains from fabrics and is particularly concerned with the removal of these stains using peroxygen bleaches at temperatures $\leqq$ about 60° C. such as are encountered in domestic washing and laundering operations.

BACKGROUND TO THE INVENTION

The removal of oxidisable stains from either hard surfaces or fabrics by means of peroxygen bleaches at temperatures less than about 60° C. is a well known technique and customarily involves the use of organic peroxy acids. The most commonly used peroxy acid is peracetic acid, normally generated in situ in the bleaching or laundry liquor by the reaction of alkaline hydrogen peroxide with a peroxy acid precursor (the so-called bleach acivator). However, peroxyacids containing more than 2 carbon atoms in the acyl group have also been disclosed and taught for this purpose and BP 864,798, Canadian Pat. No. 635,620, U.S. Pat. Nos. 4,100,095, 4,119,660, 4,126,573 and European Published Application No. 0068547 all relate to the formation, stabilisation or use of such materials.

Recently, as described in European Published Application No. 0068547, it has been found that selection of the chainlength of the aliphatic moiety of the peroxy acid permits the peroxy acid to be concentrated in the area where stain removal is required. Thus for removal of fugitive dyestuffs in bulk solution, a 'hydrophilic' bleach species is satisfactory, whereas for stains on solid surfaces a bleaching species showing more hydrophobic character, and hence a tendency to migrate to the solid-liquid interface, may be more beneficial.

In the commonly assigned U.S. Pat. No. 4,412,934 issued to Stanley Y Chung & Gianfranco L Spadini, on Nov. 1st 1983 entitled "Bleaching Compositions", and Published European Application No. 83303675.9 entitled "Detergent Additive Product", compositions are disclosed which incorporate a $C_8$–$C_{10}$ acyloxy compound capable of forming a $C_8$–$C_{10}$ aliphatic peroxy acid on reaction with alkaline hydrogen peroxide, the $C_8$–$C_{10}$ acyl group being linear in nature.

Although compositions prepared in accordance with these last named disclosures provide superior stain removal performance to prior art products employing peracetic acid or its precursors, it has been found that, under certain conditions, odors produced in the wash solution by these products are aesthetically unattractive.

It has now been found that certain branched chain aliphatic peroxy acid precursors, when added to aqueous liquors containing a source of alkaline hydrogen peroxide, provide effective bleaching of oxidisable stains, particularly at temperatures at or below about 60° C. without generating aesthetically unattractive odours. The precursor compounds can be added to such liquors on their own, or added to water as part of a complete inorganic peroxy bleach-containing detergent composition or as part of a laundry additive product added to an aqueous solution of an inorganic peroxy bleach-containing detergent composition.

SUMMARY OF THE INVENTION

According to one aspect of the invention therefore there is provided a non linear aliphatic peroxycarboxylic acid precursor adapted to form a non linear aliphatic peroxy acid in aqueous alkaline hydrogen peroxide solution wherein the precursor has the general formula:

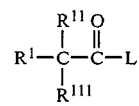

wherein the group:

is an organic moiety of non linear structural configuration, $R^{II}$ and $R^{III}$ being independently selected from hydrogen and $C_1$–$C_4$ alkyl groups, the group:

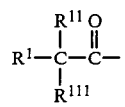

being the acyl moiety of a carboxylic acid having a log $P_{oct}$ of from about 1.9 to about 4.1, wherein $P_{oct}$ is the partition coefficient of the carboxylic acid between n-octanol and water at 21° C., and L is a leaving group having a formula selected from the group consisting of

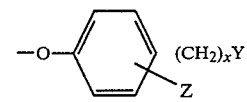

(a)

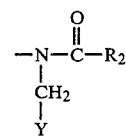

(b)

wherein Z is selected from the group consisting of H, $R_2$ and halide; $R_2$ is an alkyl group containing from 1 to about 4 carbon atoms; x is 0 or an integer from 1 to 4 and Y is selected from the group consisting of:
 —$SO_3M$
 —$OSO_3M$
 —$CO_2M$
 —$N^+(R_2)_3Q^-$
 —$N(R_2)_2{\to}O$
wherein M is selected from the group consisting of H, alkali metal, alkali earth metal ammonium or substituted ammonium; and Q is halide or methosulphate.

These leaving groups have a pKa in the range from about 6 to about 13 more preferably in the range from about 7 to about 11, most preferably from about 8 to about 10.

Preferred leaving groups are those of formula (a) above in which Z is H, X is O and Y is selected from —SO₃M and —CO₂H wherein M is alkali metal preferably sodium.

Preferably the group:

is a $C_7$–$C_9$ alkyl group and preferred compounds are alkali metal, ammonium or substituted ammonium 2-ethyl hexanoyl oxybenzene sulphonates and 3,5,5-trimethyl hexanoyl oxybenzene sulphonates, with sodium being the preferred cation.

According to another aspect of the invention, detergent compositions are provided comprising a compound, as above defined, in combination with a surfactant which may be anionic, nonionic, cationic or zwitterionic or a mixture thereof and a source of alkaline hydrogen peroxide. In a preferred form of this aspect of the invention, the surfactant is a mixture which is primarily anionic in character with nonionic and, in a highly preferred form, cationic components. Also in a preferred form of the invention, the molar ratio of the hydrogen peroxide present to the defined compound is at least about 1.5:1.

In a further aspect of the invention, laundry additive products are provided in which a compound, as hereinabove defined, is enclosed in a container such as a bag or pouch of synthetic polymeric film material which is formed with a water frangible closure to permit release of its contents on immersion in an alkaline aqueous laundry liquor containing a source of hydrogen peroxide. Another form of this aspect of the invention comprises a compound as defined above in water-releasable combination with a flexible non-particulate substrate in a weight compound:substrate ratio of about 1:10 to about 30:1. In both of these additive compositions under detergent components, such as surfactants, builder salts and chelating agents, may be present.

The invention also embraces bleaching compositions comprising an aliphatic percarboxylic acid of formula R—COOH where R is a $C_6$–$C_{16}$ alkyl group which is branched in at least the 2- and/or 3-position with respect to the carbonyl carbon atom, there being a linear alkyl chain of 5 or more carbon atoms extending from and including the carbonyl carbon in combination with a stabilising agent.

Other aspects of the invention comprise a method of forming an aqueous laundry liquor having a blend odour by the addition of laundry additive compositions as defined above to aqueous solutions containing a source of alkaline hydrogen peroxide and laundry liquors formed by such a method or by the dissolution of a detergent or bleaching composition containing a compound as defined above.

DETAILED DESCRIPTION OF THE INVENTION

The compounds found to be useful as organic peroxyacid bleach precursors have the formula

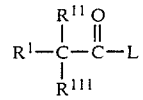

wherein the group:

is an organic moiety of non linear structural configuration, $R^{II}$ and $R^{III}$ being independently selected from hydrogen and $C_1$–$C_4$ alkyl groups, the group:

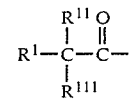

being the acyl moiety of a carboxylic acid having a log $P_{oct}$ of from about 1.9 to about 4.1, wherein $P_{oct}$ is the partition coefficient of the carboxylic acid between n-octanol and water at 21° C., and L is a leaving group the conjugate acid of which has a pKa in the range from about 6 to about 13. $R^I$ is an organic moiety which can have a variety of forms. Thus $R^I$ may be aliphatic in nature and may be linear cycloaliphatic or branched. Alternatively $R^I$ may be aromatic, alkyl aromatic or aryl aliphatic. $R^I$ may also include heteroatoms such as oxygen, nitrogen and halogen provided these are not in the backbone of the group i.e. they must be pendant from the hydrocarbyl structure. Groups subject to oxidative attack such as aldehyde groups should not be present and the moiety should preferably be free of unsaturation other than that of aromatic character. Preferably $R^I$ is a hydrocarbyl moiety.

The effects of structure on the hydrophobicity of organic compounds as represented by their partition coefficients between octanol and water are described by A Leo et al in Chemical Reviews, 71, pp 525–616 (1971) which is hereby specifically incorporated herein by reference. The authors provide numerical values for the change in Log $P_{OCT}$ (where $P_{OCT}$ is the partition coefficient between n-octanol and water) associated with the incorporation of various substituents into a range of structures. This permits a value for Log$P_{OCT}$ to be predicted for any structure.

All of the compounds display surface activity but this property is not very marked for compounds in which the group $R^I$—$C(R^{II}R^{III})$— contains less than about 8 carbon atoms and only those compounds in which $R^I$—$C(R^{II}R^{III})$— contains more than about 10 carbon atoms display detergent characteristics. Hydrocarbyl group branching confers increased solubility relative to linear compounds of the same number of carbon atoms and this increased solubility is associated with a decrease in surface activity relative to the corresponding linear compound. This effect also holds true for the aliphatic peroxy acids produced on perhydrolysis of the compounds. However, it has now surprisingly been found that aqueous liquors containing non linear aliphatic peroxy carboxylic acids in which non linearity occurs on the 2-and/or 3-carbon atoms with respect to the carbonyl carbon have a less intense odor of more aesthetically acceptable character than those containing the corresponding linear aliphatic peroxyacids. The latter characteristically have intense, pungent, and aesthetically unattractive odors which are difficult to mask using conventional detergent fragrances.

The existence of non linearity on carbon atoms further removed from the carbonyl carbon than the 3-carbon atom position also appears to be beneficial but to a lesser extent and little or no odor benefit is seen for non linearity commencing at 5- or higher carbon atom positions relative to the carbonyl carbon. Accordingly, branching on 4- and higher carbon atoms is not believed to be critical to the odor forming capability of the compound. The reason for this difference in behaviour between branched and linear aliphatic peroxy acids is not well understood and does not appear to be predictable.

The introduction of non linearity into the organic group $R^I\!-\!C(R^{II}R^{III})\!-$ also affects the rate of perhydrolysis of the precursor in alkaline hydrogen peroxide solutions. Substitution and, in particular, di substitution of an alkyl group on the 2-carbon causes a lowering in the rate of perhydrolysis of the precursor because it hinders the approach of perhydroxyl ion and is believed to reduce the effectiveness of the percarboxylic acid as a bleach. Non linearity on the 2-carbon is thus less preferred than on the 3-carbon where e.g. di alkyl substitution has much less effect on the perhydrolysis of the compound whilst still providing an aliphatic peroxy acid of improved odor.

One preferred form of the group:

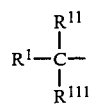

wherein $R^{II}$ and $R^{III}$ are as previously defined, is thus the group:

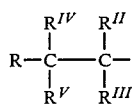

$R^{IV}$ and $R^V$ are each independently selected from hydrogen and $C_1$-$C_4$ alkyl groups and the group:

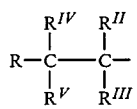

comprises a $C_6$-$C_{16}$ alkyl group in which at least one of $R^{II}$, $R^{III}$, $R^{IV}$ and $R^V$ are $C_1$-$C_4$ alkyl, there being a linear chain of five or more carbon atoms extending from and including the carbonyl carbon. Preferably $R^{II}$ and $R^{III}$ are hydrogen atoms.

Branched chain alkyl group-containing precursors in which there is no more than a single branch on the 2-carbon but at least one on the 3-carbon perhydrolyse at an adequate rate (i.e. >80% conversion within approximately 5 minutes) but still produce an odour when dissolved in an aqueous alkaline solution of hydrogen peroxide. However this odor is of a more acceptable type and level than that produced by the corresponding linear alkyl precursors under the same conditions.

A preferred number of carbon atoms in the alkyl group:

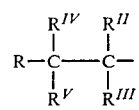

is from 7 to 9 carbon atoms with a linear chain of from 5 to 8 carbon atoms and with $R_{IV}$ and/or $R_V$ comprising a side chain i.e. in the 3-carbon position with respect to the carbonyl carbon atom.

The most preferred R group structures of this type are $C_7$-$C_9$ radicals in which there is a single methyl side chain in the 3-carbon atom position and the alkyl group is terminated by a tertiary butyl moiety.

Structures in accordance with the invention for the group

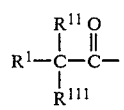

where $R^I$ is aliphatic include:

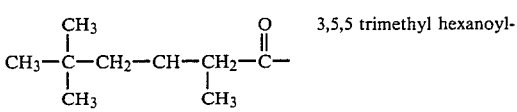 3,5,5 trimethyl hexanoyl-

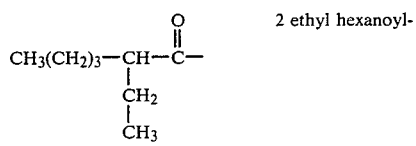 2 ethyl hexanoyl-

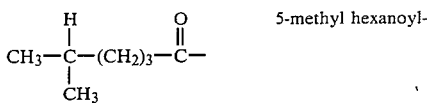 5-methyl hexanoyl-

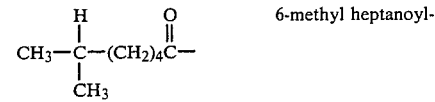 6-methyl heptanoyl-

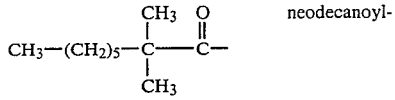 neodecanoyl-

Of the above the 3,5,5 trimethyl hexanoyl structure is the most preferred for odor and rate of perhydolysis with the 5-methyl hexanoyl, 6-methylheptanoyl and neodecanoyl structures being less preferred for odor and the neodecanoyl and 2-ethyl hexanoyl being less preferred for the rate of perhydrolysis.

Structures in accordance with the invention for the group

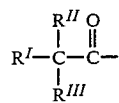

where $R^I$ incorporates a cyclo aliphatic or aromatic functionality include

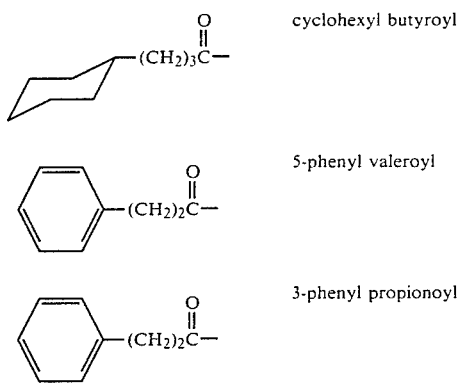

cyclohexyl butyroyl 5-phenyl valeroyl 3-phenyl propionoyl of the above, the 5-phenyl valeroyl and the 3-phenyl propionoyl structures are the most preferred, having a virtually bland odor and an acceptable rate of perhydrolysis.

The leaving group L must be capable of displacement from the bleach precursor as a consequence of the nucleophilic attack on the bleach precursor by perhydroxyl anion generated by alkaline hydrogen peroxide. This, the perhydrolysis reaction, results in the formation of the percarboxylic acid. Generally, for a group to be a suitable leaving group it must exert an electron withdrawing effect within the precursor molecule as this facilitates the nucleophilic displacement by the perhydroxyl anion.

Suitable leaving groups for this purpose have conjugate acid forms, the pKa of which should lie within the range from about 6 to about 13. pKa values above about 13 make the electron withdrawal effect so small as to be ineffective in promoting nucleophilic attack by perhydroxyl anion, an example of such a leaving group being $-OCH_3$. pKa values below about 6 reflect such a large electron withdrawal effect as to make the molecule reactive to a wide variety of materials including e.g. water. Certain aliphatic anhydrides fall into this class. Preferred leaving groups have a pKa in the range from about 7 to about 11, more preferably from about 8 to about 10.

However for the purposes of the present invention the leaving group must also confer a degree of solubility on the precursor molecule so that it partitions between the aqueous phase and any organic phase present. Certain leaving groups such as sulphonamide groups, having conjugate acid forms of the appropriate pKa, do not provide sufficient aqueous solubility to the precursor molecule and therefore do not give a sufficient rate of perhydrolysis to be practicable in a laundry detergent liquor.

The leaving groups L found to be useful in compounds of the present invention are those having the formula

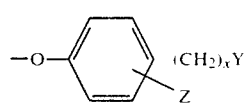
(a)

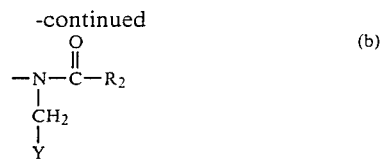
(b)

wherein Z is H, $R_2$ or halide; $R_2$ is an alkyl group containing from 1 to 4 carbon atoms; x is 0 or an integer from 1 to 4 and Y is selected from:

—$SO_3M$
—$OSO_3M$
—$CO_2M$
—$N^+(R_2)_3Q^-$
—$N(R_2)_2\rightarrow O$ wherein M is H, alkali metal, alkali earth metal ammonium or substituted ammonium; and Q is halide or methosulphate.

The preferred leaving group L has the formula (a) in which Z is H, x is O, and Y is a sulphonate, carboxylate or dimethyl amine oxide radical.

The position of the solubilising group Y on the benzene ring in formula (a) is not critical in that o-, m- and p-positions provide operable species. Nevertheless polar and steric factors make the o-substituted material most difficult to synthesise and of least value in that steric hindrance impedes the approach of perhydroxyl ion. In the preferred embodiment of leaving group L, where Y is a sulphonate radical, the precursor will normally be isolated in the form of its alkali metal salt because of the difficulty of handling the acid form.

Synthesis of the compounds of the invention can be illustrated generally by a sequence of reactions in which a $C_7$–$C_{17}$ acid or acid chloride is formed in which the acyl group has the required branched structure and the subsequent reaction of this with a compound of formula (a) above wherein the free bond is satisfied by a hydrogen atom.

The $C_7$–$C_{17}$ acid or acid chloride starting material, in which the acyl group has a linear chain of at least 5 carbon atoms extending from and including the carbonyl carbon and including a branch in at least the 2- and/or 3-carbon position, is prepared by methods known in the art.

Thus, modified OXO syntheses can be used in which alpha-olefins are reacted with carbon monoxide and water in the presence of cobalt catalysts to form a mixture of acids of which 60–65% have either 2-methyl or 2-ethyl branching. If branched olefins are used as the starting material, the resulting acids are completely branched. Branched olefins themselves, having chain lengths up to $C_{15}$, are produced by polymerising propylene or butene using a phosphoric acid catalyst under conditions of high temperature and pressure. The dimerisation of isobutene or the codimerisation of n-butene and isobutene leads to a highly branched isononanoic acid which is a preferred starting material. The olefin source for another preferred starting material, 2-ethyl hexanoic acid, is propylene, which is converted to n-butyraldehyde and thence to 2-ethyl hexanoic acid by aldol condensation of the aldehyde followed by hydrogenation of the aldol condensation product and final oxidation.

Manufacture of the acid reactant used in the preparation of sodium 3,5,5-trimethyl hexanoyl oxybenzene sulphonate, a preferred compound in accordance with the invention, involves the condensation of two moles of butene to form diisobutene followed by carbonylation to produce the aldehyde and subsequent oxidation to form the isononanoic acid. This is then converted into the acid chloride in known manner. The acid chloride is refluxed with sodium phenol sulphonate in a nitrogen current at 100°-150° C. for 10-20 hours to form the sodium 3,5,5-trimethyl hexanoyl benzene sulphonate. Alternatively, the isononanoic acid can be transesterified, refluxing at 160°-180° C. with sodium phenol sulphonate and acetic anhydride in the presence of a small amount of sodium acetate catalyst, thereafter volatilising the by-product acetic acid and precipitating the sulphonate salt product from an organic solvent. A similar reaction procedure starting with n-nonanoic acid is disclosed and claimed in the commonly assigned copending British Application No. 8227675 filed on Sept. 28, 1982, hereby specifically incorporated herein by reference.

Similar procedures to the above are also employed in the synthesis of sodium 2-ethyl hexanoyl oxybenzene sulphonate.

The analogous acyl oxybenzene carboxylate salts are also preferred compounds useful as peroxyacid bleach precursors. Synthesis of these materials is similar to that of the sulphonate salts in that the acid chloride is refluxed with p-hydroxybenzoic acid to produce the acyloxybenzoic acid product which can be recovered by addition of petroleum ether to precipitate the acid.

Sodium 3,5,5-trimethyl hexanoyl oxybenzoate and sodium 2-ethyl hexanoyl oxybenzoate are preferred members of this class of compounds. Although the above compounds are described in terms of their sodium salts, other alkali metal and alkali earth metal cations and ammonium and substituted quaternary ammonium salts such as tri $C_2$-$C_3$ alkanol ammonium salts can also be employed.

This aspect of the invention is best illustrated in the following description of the preparation of two compounds useful as organic peroxyacid bleach precursors.

(1) Synthesis of sodium 3,5,5-trimethyl hexanoyloxybenzene sulphonate

Isononanoyl chloride of purity 95.8% and molecular weight 176.5 (supplied by Akzo BV, Queens Road Hersham, Surrey, England) and sodium phenol sulphonate of purity 99.5% and MWt 196 (supplied by BDH Chemicals Ltd, Poole, Dorset, England) were used as the starting materials in the reaction.

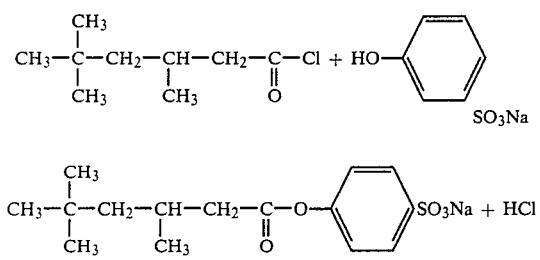

19.62 gms of finely powdered, anhydrous sodium phenol sulphonate (1/10th mole) and 22.06 gms of Akzo isononanoyl chloride (weight 1/10th mole+25% excess) are weighed into a 500 ml conical flask containing 250 mls of chlorobenzene. The flask was fitted with a magnetic stirrer, a 2-way head carrying a $N_2$ gas inlet (leading to the base of the flask) and a reflux condenser (+$CaCl_2$ tube) and was surrounded by an oil-bath. The flask was heated with stirring to 120° C. and with $N_2$ gas passing through the flask, was maintained at that temperature overnight (20 hours). The heating was then turned off and the flask contents allowed to cool to room temperature. The contents were then washed with 3×1 liter diethyl ether, filtering between each wash (a Silverson stirrer was used for agitation). The resulting white solid was dried in a vacuum oven (no heat) after which the product was ground into a fine powder and dried again in the vacuum oven.

Yield: 27.40 gms (81.5% yield)

NMR analysis showed 81.4% required compound.

(2) Synthesis of sodium 2-ethyl hexanoyl oxybenzene sulphonate

Anhydrous sodium phenol sulphonate (58.85 g; 0.3 mole) was added to a stirred mixture of acetic anhydride (36.75 g; 0.36 mole), 2-ethylhexanoic acid (129.8 g; 0.9 mole) and sodium acetate (3 g). The resultant white suspension was stirred under nitrogen and heated to 160° C. under reflux; vigorous boiling occurred and was maintained for 4.5 hours.

At this point the nitrogen lead was transferred from the condenser top to a spare inlet on the flanged-top of the reaction vessel and the condenser was set up in a distillation mode. The pot temperature was gradually increased to 260° C. during 1.5 hours; the still-head temperature rose to 131° C. The contents of the reaction pot were then allowed to cool overnight to ambient temperature before being washed with 3×1.5 liters diethyl ether, filtering between washes, and then being dried.

The yield of sodium 2-ethyl hexanoyl oxybenzene sulphonate was 88.3 g, 91.3% of theory. Purity (by cat. $SO_3$ determination)=93.4%.

A second aspect of the invention relates to detergent compositions incorporating the compounds as defined above, primarily as peroxyacid bleach precursors, (the so-called low temperature bleach activators). Such detergent compositions comprise an organic surfactant, a compound as hereinbefore defined and a source of alkaline hydrogen peroxide and are normally particulate in physical form.

A wide range of surfactants can be used in the present laundry compositions. A typical listing of the classes and species of these surfactants is given in U.S. Pat. No. 3,664,961 issued to Norris on May 23, 1972, hereby specified incorporated herein by reference.

Suitable synthetic anionic surfactants are water-soluble salts of alkyl benzene sulphonates, alkyl sulphates, alkyl polyethoxy ether sulphates, paraffin sulphonates, alpha-olefin sulphonates, alpha-sulpho-carboxylates and their esters, alkyl glyceryl ether sulphonates, fatty acid monoglyceride sulphates and sulphonates, alkyl phenol polyethoxy ether sulphates, 2-acyloxy alkane-1-sulphonate, and beta-alkyloxy alkane sulphonate.

A particularly suitable class of anionic surfactants includes water-soluble salts, particularly the alkali metal, ammonium and alkanolammonium salts of organic sulphuric reaction products having in their molecular structure an alkyl or alkaryl group containing from 8 to 22, especially from about 10 to about 20 carbon atoms and a sulphonic acid or sulphuric acid ester group. (Included in the term "alkyl" is the alkyl portion of acyl groups). Examples of this group of synthetic detergents which form part of the detergent compositions of the present invention are the sodium and potassium alkyl sulphates, especially those obtained by sulphating the higher alcohols (C$_{8-18}$) carbon atoms produced by reducing the glycerides of tallow or coconut oil and sodium and potassium alkyl benzene sulphonates, in which the alkyl group contains from about 9 to about 15, especially from about 11 to about 13, carbon atoms, in straight chain or branched chain configuration. The latter include those of the type described in U.S. Pat. No. 2,220,099 and U.S. Pat. No. 2,477,383 (hereby specifically incorporated herein by reference) and those prepared from alkylbenzenes obtained by alkylation with straight chain chloroparaffins (using aluminium trichloride catalysis) or straight chain olefins (using hydrogen fluoride catalysis). Especially valuable are linear straight chain alkyl benzene sulphonates in which the average of the alkyl group is 11.8 carbon atoms, abbreviated as C$_{11.8}$ LAS, and C$_{12}$–C$_{15}$ methyl branched alkyl sulphates.

Other anionic detergent compounds herein include the sodium C$_{10-18}$ alkyl glyceryl ether sulphonates, especially those ethers of higher alcohols derived from tallow and coconut oil; sodium coconut oil fatty acid monoglyceride sulphonates and sulphates; and sodium or potassium salts of alkyl phenol ethylene oxide ether sulphate containing from 1 to about 10 units of ethylene oxide per molecule and wherein the alkyl groups contain from about 8 to about 12 carbon atoms.

Other useful anionic detergent compounds herein include the water-soluble salts or esters of alpha-sulphonated fatty acids containing from about 6 to about 20 carbon atoms in the fatty acid group and from about 1 to about 10 carbon atoms in the ester group; water-soluble salts of 2-acyloxy-alkane-1-sulphonic acids containing from about 2 to about 9 carbon atoms in the acyl group and from about 9 to about 23 carbon atoms in the alkane moiety; alkyl ether sulphates containing from about 10 to about 18, especially from about 12 to about 16, carbon atoms in the alkyl group and from 1 to about 12, especially from 1 to about 6, more especially from 1 to about 4 moles of ethylene oxide; water-soluble salts of olefin sulphonates containing from about 12 to about 24, preferably from about 14 to about 16, carbon atoms, especially those made by reaction with sulphur trioxide followed by neutralization under conditions such that any sultones present are hydrolysed to the corresponding hydroxy alkane sulphonates; water-soluble salts of paraffin sulphonates containing from about 8 to about 24, especially from about 14 to about 18 carbon atoms, and beta-alkyloxy alkane sulphonates containing from 1 to about 3 carbon atoms in the alkyl group and from about 8 to about 20 carbon atoms in the alkane moiety.

The alkane chains of the foregoing non-soap anionic surfactants can be derived from natural sources such as coconut oil or tallow, or can be made synthetically as for example using the Ziegler or Oxo processes. Water solubility can be achieved by using alkali metal, ammonium or alkanolammonium cations; sodium is preferred. Suitable fatty acid soaps can be selected from the ordinary alkali metal (sodium, potassium), ammonium, and alkylolammonium salts of higher fatty acids containing from about 8 to about 24, preferably from about 10 to about 22 and especially from about 16 to about 22 carbon atoms in the alkyl chain. Suitable fatty acids can be obtained from natural sources such as, for instance, from soybean oil, castor oil, tallow, whale and fish oils, grease, lard and mixtures thereof). The fatty acids also can be synthetically prepared (e.g., by the oxidation of petroleum, or by hydrogenation of carbon monoxide by the Fischer-Tropsch process). Resin acids are suitable such as rosin and those resin acids in tall oil. Naphthenic acids are also suitable. Sodium and potassium soaps can be made by direct saponification of the fats and oils or by the neutralization of the free fatty acids which are prepared in a separate manufacturing process. Particularly useful are the sodium and potassium salts of the mixtures of fatty acids derived from tallow and hydrogenated fish oil.

Mixtures of anionic surfactants are particularly suitable herein, especially mixtures of sulphonate and sulphate surfactants in a weight ratio of from about 5:1 to about 1:5, preferably from about 5:1 to about 1:2, more preferably from about 3:1 to about 2:3. Especially preferred is a 1:1 mixture of an alkyl benzene sulphonate having from about 9 to about 15, especially from about 11 to about 13 carbon atoms in the alkyl radical, the cation being an alkali metal, preferably sodium; and either an alkyl sulphate having from about 12 to about 18, preferably from about 14 to about 16 carbon atoms in the alkyl radical or an ethoxy sulphate having from about 10 to about 20, preferably from about 10 to about 16 carbon atoms in the alkyl radical and an average degree of ethoxylation of from about 1 to about 6, having an alkali metal cation, preferably sodium.

The nonionic surfactants useful in the present invention are condensates of ethylene oxide with a hydrophobic moiety to provide a surfactant having an average hydrophilic-lipophilic balance (HLB) in the range from about 8 to about 17, preferably from about 9.5 to about 13.5, more preferably from about 10 to about 12.5. The hydrophobic moiety may be aliphatic or aromatic in nature and the length of the polyoxyethylene group which is condensed with any particular hydrophobic group can be readily adjusted to yield a water-soluble compound having the desired degree of balance between hydrophilic and hydrophobic elements.

Examples of suitable nonionic surfactants include:
1. The polyethylene oxide condensates of alkyl phenol, e.g. the condensation products of alkyl phenols having an alkyl group containing from about 6 to about 12 carbon atoms in either a straight chain or branched chain configuration, with ethylene oxide, the said ethylene oxide being present in amounts equal to from about 3 to about 30, preferably from about 5 to about 14 moles of ethylene oxide per mole of alkyl phenol. The alkyl substituent in such compounds may be derived, for example, from polymerised propylene, di-isobutylene, octene and nonene. Other examples include dodecylphenol condensed with an average of abut 9 moles of ethylene oxide per mole of phenol; dinonylphenol condensed with an average of about 11 moles of ethylene oxide per mole of phenol; nonylphenol and di-isooctylphenol condensed with an average of about 13 moles of ethylene oxide.
2. The condensation product of primary or secondary aliphatic alcohols having from about 8 to about 24 carbon atoms, in either straight chain or branched chain configuration, with from about 2 to about 40 moles, preferably from about 2 to about 9 moles of ethylene oxide per mole of alcohol. Preferably, the aliphatic alcohol comprises between about 9 and about 18 carbon atoms and is ethoxylated with an average of between 2 and 9, desirably between 3 and 8 moles of ethylene oxide per mole of aliphatic alcohol. The preferred surfactants are prepared from primary alcohols which are either linear (such as those derived from natural fats or, prepared by the Ziegler process from ethylene, e.g. myristyl, acetyl, stearyl alcohols), or partly branched such as the Lutensols, Dobanols and Neodols which have about 25% 2-methyl branching (Lutensol being a Trade Name of BASF, Dobanol and Neodol being Trade Names of Shell), or Synperonics, which are understood to have about 50% 2-methyl branching (Synperonic is a Trade Name of I.C.I.) or the primary alcohols having more than 50% branched chain structure sold under the Trade Name Lial by Liquichimica. Specific examples of nonionic surfactants useful for the purposes of the invention include Dobanol 45-4, Dobanol 45-7, Dobanol 45-9, Dobanol 91-2.5, Dobanol 91-3, Dobanol 91-4, Dobanol 91-6, Dobanol 91-8, Dobanol 23-6.5, Synperonic 6, Synperonic 14, the condensation products of coconut alcohol with an average of between 5 and 12 moles of ethylene oxide per mole of alcohol, the coconut alkyl portion having from 10 to 14 carbon atoms, and the condensation products of tallow alcohol with an average of between 7 and 12 moles of ethylene oxide per mole of alcohol, the tallow portion comprising essentially between 16 and 22 carbon atoms. Secondary linear alkyl ethoxylates are also suitable in the present compositions, especially those ethoxylates of the Tergitol series having from about 9 to about 15 carbon atoms in the alkyl group and up to about 11, especially from about 3 to about 9, ethoxy residues per molecule.

Useful nonionic surfactants also include those in which ethylene oxide is condensed with a hydrophobic base formed by the condensation of propylene oxide with propylene glycol wherein the molecular weight of the hydrophobic portion generally falls in the range of from about 1500 to about 1800. Such synthetic nonionic detergents are available on the market under the Trade Name of "Pluronic" supplied by Wyandotte Chemicals Corporation.

Especially preferred nonionic surfactants for use herein are the $C_9$–$C_{15}$ primary alcohol ethoxylates containing an average of about 3–8 moles of ethylene oxide per mole of alcohol, particularly the $C_{12}$–$C_{15}$ primary alcohols containing an average of 6–8 moles of ethylene oxide per mole of alcohol.

Cationic surfactants suitable for use herein include quaternary ammonium surfactants and surfactants of a semi-polar nature, for example amine oxides. Suitable quaternary ammonium surfactants are selected from mono $C_8$–$C_{16}$, preferably $C_{10}$–$C_{14}$ N-alkyl or alkenyl ammonium surfactants wherein remaining N positions are substituted by methyl, hydroxyethyl or hydroxypropyl. Suitable amine oxides are selected from mono $C_8$–$C_{20}$, preferably $C_{10}$–$C_{14}$ N-alkyl or alkenyl amine oxides and propylene-1,3-diamine dioxides wherein the remaining N positions are again substituted by methyl, hydroxyethyl or hydroxypropyl.

The detergent compositions can comprise from 1%–70% by weight of surfactant, but usually the surfactant is present in an amount of from about 1% to about 20%, more preferably from about 5% to about 15% by weight. Mixtures of surfactant types are preferred, particularly anionic-cationic mixtures. Particularly preferred mixtures are described in British Pat. No. 2040987 and Bleil et al. U.S. Application Ser. Nos. 353,743 filed Mar. 1, 1982, and 380,987 filed May 24, 1982, the disclosures of said documents being hereby incorporated herein by reference.

A source of hydrogen peroxide can be provided by any of the commercially available inorganic peroxygen bleaches and also by certain hydrogen peroxide adducts.

Suitable inorganic peroxygen bleaches include sodium perborate mono and tetra hydrate, sodium percarbonate, sodium persilicate and the clathrate $4Na_2SO_4:2H_2O_2:1NaCl$. A separate source of alkalinity is required for clathrate materials and for stability reasons this should preferably be kept physically separated from the hydrogen peroxide source by e.g. enrobing or encapsulating the latter. The hydrogen peroxide source will normally be present in an amount of from about 1% to about 40%, more preferably from about 5% to about 35% by weight of the composition and will most frequently be present in an amount of from about 10% to about 30% by weight.

In preferred embodiments of this aspect of the invention the levels of hydrogen peroxide source and precursor compound are arranged so that the molar ratio of hydrogen peroxide yielded by the source to precursor compound is greater than about 1.5:1, normally at least about 2.0:1. Under the usage conditions encountered in domestic European laundry practice, this molar ratio is generally greater than about 5.0:1 and most preferably is greater than about 10:1.

Preferred detergent compositions, in accordance with the invention, will include these components commonly included in heavy duty laundry detergents such as suds suppressing detergent builders, chelating agents, soil suspending and anti redeposition agents, optical brightening agents, enzymes, colours and perfumes.

Suds suppressors useful in the detergent composition aspect of the invention, particularly compositions used in laundering fabrics, are represented by materials of the silicone, wax, vegetable and hydrocarbon oil and phosphate ester varieties. Suitable silicone suds controlling agents include polydimethylsiloxanes-having a molecular weight in the range from about 200 to about 200,000 and a kinematic viscosity in the range from about 20 to about 2,000,000 $mm^2/s$ (cSt), preferably from about 3000 to about 30,000 $mm^2/s$ (cSt), and mixtures of siloxanes and hydrophobic silanated (preferably trimethylsilanted) silica having a particle size in the range from about 10 millimicrons to about 20 millimicrons and a specific surface area above about 50 $m^2/g$. Suitable waxes include microcrystalline waxes having a melting point in the range from about 65° C. to about 100° C., a molecular weight in the range from 4,000–10,000, and a penetration value of at least about 6, measured at 77° C. by ASTM-D1321, and also paraffin waxes, synthetic waxes and natural waxes. Suitable phosphate esters include mono- and/or di-$C_{16}$–$C_{22}$ alkyl or alkenyl phosphate esters, and the corresponding mono- and/or di alkyl or alkenyl ether phosphates containing up to about 6 ethoxy groups per molecule.

Suds suppressors are normally included at levels of from about 0.01% to about 5% by weight of the composition, dependent on the type of suds suppressor used, more commonly from about 0.1% to about 2% by weight.

A highly preferred component of detergent compositions in accordance with the invention is one or more detergent builder salts which may comprise up to about 90% of the composition, more typically from about 10% to about 70% by weight thereof. Suitable detergent builder salts useful herein can be of the polyvalent inorganic and polyvalent organic types, or mixtures thereof. Non-limiting examples of suitable water-soluble, inorganic alkaline detergent builder salts include the alkali metal carbonates, borates, phosphates, pyrophosphates, tripolyphosphates and bicarbonates.

Examples of suitable organic alkaline detergency builder salts are water-soluble polycarboxylates such as the salts of nitrilotriacetic acid, lactic acid, glycollic acid and ether derivatives thereof as disclosed in BE-A-821,368, 821,369 and 821,370; succinic acid, malonic acid, (ethylenedioxy)diacetic acid, maleic acid, diglycollic acid, tartaric acid, tartronic acid and fumaric acid; citric acid, aconitric acid, citraconic acid, carboxymethyloxysuccinic acid, lactoxysuccinic acid, and 2-oxy-1,1,3-propane tricarboxylic acid; oxydisuccinic acid, 1,1,2,2-ethane tetracarboxylic acid, 1,1,3,3-propane tetracarboxylic acid and 1,1,2,3-propane tetracarboxylic acid; cyclopentane cis, cis,cis-tetracarboxylic acid, cyclopentadiene pentacarboxylic acid, 2,3,4,5-tetrahydrofuran-cis, cis, cis-tetracarboxylic acid, 2,5-tetrahydrofuran-cis-dicarboxylic acid, 1,2,3,4,5,6-hexanehexacarboxylic acid, mellitic acid, pyromellitic acid and the phthalic acid derivatives disclosed in GB-A-1,425,343.

Mixtures of organic and/or inorganic builders can be used herein. One such mixture of builders is disclosed in CA-A-755,038, e.g. a ternary mixture of sodium tripolyphosphate, trisodium nitrilotriacetate, and trisodium ethane-1-hydroxy-1,1-diphosphonate.

A further class of builder salts is the insoluble alumino silicate type which functions by cation exchange to remove polyvalent mineral hardness and heavy metal ions from solution. A preferred builder of this type has the formulation $Na(AlO_2)_z(SiO_2)_y \cdot xH_2O$ wherein z and y are integers of at least 6, the molar ratio of z to y is in the range from 1.0 to 0.5 and x is an integer from 15 to 264. Compositions incorporating builder salts of this type form the subject of GB-A-1,429,143 published Mar. 24, 1976, DE-A-2,433,485 published Feb. 6, 1975 and DE-A-2,525,778 published Jan. 2, 1976. All of the mentioned patents relating to builder salts are hereby specifically incorporated herein by reference.

An alkali metal, or alkaline earth metal, silicate can also be present. The alkali metal silicate is preferably from 3% to 15%. Suitable silicate solids have a molar ratio of $SiO_2$/alkali metal$_2O$ in the range from 1.0 to 3.3, more preferably from 1.5 to 2.0.

Chelating agents that can be incorporated include citric acid, nitrilotriacetic and ethylene diamine tetra acetic acids and their salts, organic phosphonate derivatives such as those disclosed in Diehl U.S. Pat. No. 3,213,030 issued Oct. 19, 1965; Roy U.S. Pat. No. 3,422,021 issued Jan. 14, 1968; Gedge U.S. Pat. No. 3,392,121 issued Jan. 9, 1968; and Bersworth U.S. Pat. No. 2,599,807 issued June 10, 1952, and carboxylic acid builder salts such as those disclosed in Diehl U.S. Pat. No. 3,308,067 issued Mar. 7, 1967, all of the above-mentioned patents being hereby specifically incorporated herein by reference. Preferred chelating agents include nitrilotriacetic acid (NTA), nitrilotrimethylene phosphonic acid (NTMP), ethylene diamine tetra methylene phosphonic acid (EDTMP) and diethylene triamine penta methylene phosphonic acid (DETPMP), and these are incorporated in amounts of from about 0.1% to about 3%, more preferably from about 0.2% to about 2% by weight of the composition.

Antiredeposition and soil suspension agents suitable herein include cellulose derivatives such as methylcellulose, carboxymethylcellulose and hydroxyethylcellulose, and homo-or co-polymeric polycarboxylic acids or their salts in which the polycarboxylic acid comprises at least two carboxyl radicals separated from each other by not more than two carbon atoms. Polymers of this type are disclosed in GB-A-1,596,756, such disclosures being specifically incorporated herein by reference. Preferred polymers include copolymers or salts thereof of maleic anhydride with ethylene, methylvinyl ether, acrylic acid or methacrylic acid, the maleic anhydride constituting at least about 20 mole percent of the copolymer. These polymers are valuable for improving whiteness maintenance, fabric ash deposition, and cleaning performance on clay, proteinaceous and oxidizable soils in the presence of transition metal impurities.

Enzymes suitable for use herein include those discussed in U.S. Pat. No. 3,519,570 and U.S. Pat. No. 3,533,139 to McCarty and McCarty et al. issued July 7, 1970 and Jan. 5, 1971, respectively. Photoactivators are discussed in EP-A-57088, highly preferred materials being zinc phthalocyanine tri- and tetra-sulphonates. The disclosures of each of these patents are specifically incorporated herein by reference.

Anionic or nonionic optical brighteners are also preferred ingredients of detergent compositions in accordance with the invention, being normally present at levels of from about 0.01% to about 1% by weight, more preferably at levels of from about 0.02% to about 0.5% by weight.

Anionic fluorescent brightening agents are well-known materials, examples of which are disodium 4,4'-bis-(2-diethanolamino-4-anilino-s-triazin-6-ylamino)stilbene-2:2'disulphonate, disodium 4,4'-bis-(2-morpholino-4-anilino-s-triazin-6-ylaminostilbene-2:2'-disulphonate, disodium 4,4'-bis-(2,4-dianilino-s-triazin-6-ylamino)stilbene-2:2'-di-sulphonate, disodium 4,4'-bis-(2-anilino-4-(N-methyl-N-2-hydroxyethylamino)-s-triazin-6-ylamino)stilbene-2,2'-di-sulphonate, disodium 4,4'-bis-(4-phenyl-2,1,3-triazol-2-yl)-stilbene-2,2'-disulphonate, disodium 4,4'-bis(2'-anilino-4-(1-methyl-2-hydroxyethylamino)-s-triazin-6-ylamino)stilbene-2,2'disulphonate, sodium 2(stilbyl-4''-(naptho-1',2':4,5)-1,2,3-triazole-2''-sulphonate and di-sodium 4,4'-bis(2-sulphonato styryl)biphenyl.

Other fluorescers to which the invention can be applied include the 1,3-diaryl pyrazolines and 7-alkylaminocoumarins.

A preferred fluorescer is the anionic material available from Ciba Geigy S.A. under the trade name Tinopal CBS and mixtures thereof with materials available under the trade names Tinopal EMS and Blankophor MBBN, the latter being sold by Farbenfabriken Bayer AG.

The non-linear aliphatic peroxy acid precursors of the present invention are normally employed at levels of from about 1% to about 15% by weight more preferably at from about 1% to about 10% and most frequently at from about 2% to about 5% by weight of the detergent composition. They can be incorporated into a detergent composition in a number of ways, most if not all of which are intended to minimise any reaction between the precursor and other components during storage prior to use.

Thus the precursor may be formed into particulates by spray cooling, prilling, marumerising, agglomeration or granulation, either alone or together with a carrier material which may be organic or inorganic in type. Suitable inorganic materials include clays and other natural and synthetic aluminosilicates, as well as hydratable salts such as phosphates, carbonates and sulphates. Suitable organic materials include ethoxylated $C_{12}$–$C_{18}$ alcohols and alkyl phenols, polyethylene glycols of MWT 4,000–10,000, $C_{12}$–$C_{18}$ fatty acids and esters thereof with monohydric and polyhydric alcohols. In one preferred method of manufacturing the precursor, disclosed in European Patent Application No. 83305621.5, filed Sept. 22, 1982, the liquid reaction product containing the precursor is blended with the carrier material under an inert gas atmosphere before being processed further to form the particulate material to be added to the detergent. This technique is particularly suitable when the carrier is a waxy organic solid such as an ethoxylated alcohol or ester and a highly preferred example, employing a glyceryl mono $C_{10}$–$C_{14}$ fatty acid ester carrier is disclosed in the Applicants' British Patent Application No. 8323127 filed Aug. 27, 1983.

In another method of manufacturing the preferred alkali metal $C_7$–$C_9$ branched chain acyl oxybenzene sulphonate phenol sulphonate precursors, one of the reaction components e.g. alkali metal phenol sulphonate or fatty acid is employed in a greater excess than is necessary to achieve the desired completeness of reaction. The excess reactant is used as a binder material for the reaction product which is taken from the reactor and, without separate crystallisation or solvent extraction steps, is compacted to form particulates which can be added directly to the detergent composition.

Preferred methods of making a particulate from a mixture of precursor and an organic carrier or builder are disclosed in the Applicants' European Application No. 83306046.0 filed Oct. 5th 1983 and their Published European Application No. 62523, both disclosures being hereby specifically incorporated herein by reference.

Particulates incorporating the precursors of the present invention are normally added to the spray dried portion of the detergent composition with the other dry-mix ingredients such as enzymes, inorganic peroxygen bleaches and suds suppressors. It will be appreciated however that the detergent composition to which the precursor particulates are added may itself be made in a variety of ways such as dry-mixing, agglomeration extrusion, flaking, etc., such ways being well known to those skilled in the art and not forming part of the present invention.

A further aspect of the invention relates to detergent additive products incorporating aliphatic peroxy acid precursors whose carboxylic acid analogues have a log $P_{OCT}$ of from about 1.9 to about 4.1. Such additive products are intended to supplement or boost the performance of conventional detergent compositions and may contain any of the components of such compositions, although they will not comprise all of the components present in a fully formulated detergent composition. Additive products in accordance with this aspect of the invention will normally be added to an aqueous liquor containing a source of (alkaline) hydrogen peroxide, although under certain circumstances a source of alkaline hydrogen peroxide may be included in the product.

Additive products in accordance with this aspect of the present invention may comprise the compound alone in combination with a carrier such as a compatible particulate substrate, a flexible non particulate substrate or a container. Examples of compatible particulate substrates include inert materials such as clays and other aluminosilicates including zeolites both natural and synthetic in organic. Other compatible particulate carrier materials include hydratable inorganic salts such as phosphates, carbonates and sulphates.

Additive products enclosed in bags or containers are manufactured such that the containers prevent egress of their contents when dry but are adapted to release their contents on immersion in an aqueous solution.

A convenient execution of this form of the additive product comprises a particulate solid compound as hereinbefore defined enclosed in a container. Usually the container will be flexible, such as a bag or pouch. The bag may be of fibrous construction coated with a water impermeable protective material so as to retain the contents, such as is disclosed in European published Patent Application No. 0018678. Alternatively it may be formed of a water insoluble synthetic polymeric material provided with an edge seal or closure designed to rupture in aqueous media as disclosed in European published Patent Application Nos. 0011500, 0011501, 0011502, and 0011968. A convenient form of water frangible closure comprises a water soluble adhesive disposed along and sealing one edge of a pouch formed of a water impermeable polymeric film such as polyethylene or polypropylene.

An alternative form of the additive product comprises a compound as hereinbefore defined in water releasable combination with a non particulate flexible substrate in a weight ratio of 1:10 to 30:1. Additive products of this type are disclosed in British Patent Specification Nos. 1,586,769 and 2040983B and also in the previously mentioned British Patent Application No. 8218867, all specifically incorporated herein by reference.

The substrate may itself be water soluble or water insoluble and in the latter case it should possess sufficient structural integrity under the conditions of the wash to be recovered from the machine at the end of the laundry cycle. Structures which are water disintegratable, i.e. that break down in aqueous media to insoluble individual fibres or particles are considered less satisfactory for the purposes of the present invention.

Water soluble materials include certain cellulose ethers, alginates, polyvinyl alcohol and water soluble polyvinyl pyrrolidone polymers, which can be formed into non-woven and woven fibrous structures. Suitable water insoluble materials include, but are not restricted to, natural and synthetic fibres, foams, sponges and films.

The substrate may have any one of a number of physical forms such as sheets, blocks, rings, balls, rods or tubes. Such forms should be amenable to unit usage by the consumer, i.e. they should be capable of addition to the washing liquor in measured amounts, such as individual sheets, blocks or balls and unit lengths of rods or tubes. Certain of these substrate types can also be adapted for single or multiple uses, and can be provided with loadings of organic peroxy acid precursor up to a precursor:substrate ratio of 30:1 by weight.

One such article comprises a sponge material releasably enclosing enough organic peroxy compound precursor to provide bleaching action during several washing cycles. This multi-use article can be made by impregnating a sponge ball or block with about 20 grams of the precursor and any adjuncts therewith. In use, the precursor leaches out through the pores of the sponge into the wash liquor and reacts with the inorganic peroxy bleach. Such a filled sponge can be used to treat several loads of fabrics in conventional washing machines, and has the advantage that it can remain in the washer after use.

A highly preferred execution of this type of additive product utilises a flexible sheet so as to make it compatible with the movement of the fabrics in the washing machine and to facilitate its handling during manufacture of the product. Preferably the sheet is water pervious i.e. water can pass from one surface of the sheet to the opposite surface and, for film type substrates, perforation of the sheet is desirable. The most preferred form of the substrate is a sheet of woven or non-woven fabric or a thin sheet of cellular plastics material. Woven fabric sheets can take the form of a plain weave natural or synthetic fibre of low fibre count/unit length, such as is used for surgical dressings, or of the type known as cheese cloth. Loading limitations on sheet type substrates limit the amount of precursor compound that can be applied to the sheet and, in practice, the weight ratio of precursor compound:sheet substrate normally lies within the range from about 1:2 to about 10:1.

Variations on the above sheet substrate product forms are also contemplated for the purposes of the present invention. For example, laminated sheet products can be employed in which a central layer is impregnated and/or coated with a composition incorporating the bleach precursor and then one or more outer layers are applied to produce a fabric-like aesthetic effect. The layers may be sealed together as as to remain attached during use or may separate on contact with water to facilitate the release of the coated or impregnated material.

An alternative laminate form comprises one layer embossed or deformed to provide a series of pouch-like containers into each of which the bleach precursor and optionally other detergent components are deposited in measured amounts, with a second layer overlying the first layer and sealed thereto in those areas between the pouch-like containers where the two layers are in contact. The bleach precursor and any accompanying components may be deposited in particulate, paste or molten form and the laminate layers should prevent egress of the contents of the pouch-like containers prior to their addition to water. The layers may separate or may remain attached together on contact with water, the only requirement being that the structure should permit rapid release of the contents of the pouch-like containers into solution. The number of pouch-like containers per unit area of substrate is a matter of choice but will normally vary between about 500 and about 25,000 per square meter.

As stated above, suitable materials which can be used as a substrate in the invention herein include, among others, sponges, paper, and woven and non-woven fabrics.

A suitable sponge like material that can be used in the present invention comprises an absorbent foam like material in the form of a sheet. The term 'absorbent foam-like material' is intended to encompass three dimensional absorptive materials such as 'gas blown foams', natural sponges and composite fibrous based structures such as are disclosed in U.S. Pat. Nos. 3,311,115 and 3,430,630, both specifically incorporated herein by reference. A particularly suitable material of this type is a hydrophilic polyurethane foam in which the internal cellular walls of the foam have been broken by reticulation. Foams of this type are described in detail in Dulle U.S. Pat. No. 3,794,029, also specifically incorporated herein by reference. A preferred example of this foam type comprises a hydrophilic polyurethane foam of density 0.596 grs per cubic inch with a cell count of between about 8 and about 40 cells per cm, preferably from about 24 to about 32 per cm available from the Scott Paper Company, Eddystone, Pa. USA., under the Registered Trade Mark "Hydrofoam". Preferred sheets of this type of material have thicknesses in the range from about 3 to about 5 mm.

Preferred sheet substrates for use in this type of additive product are apertured and non apertured non woven fabrics which can generally be defined as adhesively bonded fibrous or filamentous product, having a web or carded fibre structure (where the fibre strength is suitable to allow carding) or comprising fibrous mats, in which the fibres or filaments are distributed haphazardly or in random array (i.e. an array of fibres in a carded web wherein partial orientation of the fibres is frequently present as well as a completely haphazard distributional orientation) or substantially aligned. The fibres or filaments can be natural (e.g. wool, silk, wood pulp, jute, hemp, cotton, linen, sisal, or ramie), synthetic (e.g. rayon, cellulose, ester, polyvinyl derivatives, polyolefins, polyamides, or polyesters) or mixtures of any of the above.

The choice of binder-resins used in the manufacture of non-woven cloths can provide substrates possessing a variety of desirable traits. For example, the absorbent capacity of the cloth can be increased, decreased, or regulated by respectively using a hydrophilic binder-resin, a hydrophobic binder-resin or a mixture thereof in the fibre bonding step. Moreover, the hydrophobic binder-resin, when used singly or as the predominant compound of a hydrophobic-hydrophilic mixture, provides non-woven cloths which are especially useful as substrates when the precursor-substrate combinations disclosed herein are used in an automatic washer.

When the substrate herein is a bonded non-woven cloth made from fibres, deposited haphazardly or in random array on the screen, the compositions exhibit excellent strength in all directions and are not prone to tear or separate when used in the washer.

Preferably, the non-woven cloth is water-laid or air-laid and is made from cellulosic fibres, particularly from regenerated cellulose or rayon, which are lubricated with standard textile lubricant. Preferably the fibres are from about 4 to about 50 mm in length and are from about 1.5 to about 5 denier (Denier is an internationally recognised unit in yarn measure, corresponding to the weight in grams of a 9,000 meter length of yarn). Preferably the fibres are at least partially orientated haphazardly, particularly substantially haphazardly, and are adhesively bonded together with hydrophobic or substantially hydrophobic binder-resin, particularly with a nonionic self-crosslinking acrylic polymer or polymers. Conveniently, the cloth comprises about 70% fibre and about 30% binder-resin polymer by weight and has a basis weight of from about 10 to about 100, preferably from about 24 to about 72 g/m$^2$.

Apertured non-woven substrates are also useful for the purposes of the present invention. The apertures, which extend between opposite surfaces of the substrate are normally in a pattern and are formed during laydown of the fibres to produce the substrate. Exemplary apertured non-woven substrates are disclosed in U.S. Pat. Nos. 3,741,724, 3,930,086 and 3,750,237, said disclosures being specifically incorporated herein by reference.

A suitable diamond patterned apertured substrate is obtainable from Chicopee Manufacturing Co., Milltown, N.J., USA under the Code No. SK 650 WFX 577 and comprising a polyester-wood pulp mixture having a basis weight of 50 g/m² and approximately 13 apertures per square cm.

Another preferred example of an apertured non-woven substrate, also available from Chicopee Manufacturing Co., under the Code No. AK 30 ML 1397 comprises a regenerated cellulose sheet of 3.0 denier fibres bonded with Rhoplex RA 8 binder (fibre:binder ratio 70:30) having a basis weight of about 40 g/m² and 17 apertures/cm². A highly preferred square patterned apertured substrate of similar composition but fibre:binder ratio of 80:20 and basis weight about 35 g/m² is also available from Chicopee BV Holland.

In general, apertured fabrics for the purposes of the invention have from about 10 to about 20 apertures/cm², preferably from about 12 to about 18 apertures/cm².

The size and shape of the substrate sheet is a matter of choice and is determined principally by factors associated with the convenience of its use. Thus the sheet should not be so small as to become trapped in the crevices of the machine or the clothes being washed or so large as to be awkward to package and dispense from the container in which it is sold. For the purposes of the present invention sheets ranging in plan area from about 130 cm² to about 1300 cm² are acceptable, the preferred area lying in the range of from about 520 cm² to about 780 cm².

Additive products in particulate substrate form can comprise powders, flakes, chips, tablets or noodles which may be used as-is or may themselves be enclosed in containers for addition to an aqueous liquor.

More usually, additive products in accordance with the invention contain other detergent ingredients in addition to the hereinbefore defined compounds.

The type and level of such optional materials is constrained only by the requirements of unreactivity towards the precursor, and, where a substrate is utilised as the, or a carrier, by the loading limitations of the substrate. This imposes a maximum weight ratio of optional ingredients to substrate of about 10:1, and in the case of coated sheet substrates of about 8:1. As described in more detail hereinafter, materials that are capable of reaction with the precursor can be incorporated in additive products of the present invention but it is essential that the precursor is spatially separate therefrom, i.e. is disposed at a substrate location that is free or substantially free of the other reactant materials.

One factor determining the acceptable level of incorporation of an optional ingredient is its physical characteristics i.e. whether it is liquid or solid and if solid whether it is crystalline or waxy and of high or low melting or softening point.

Highly desirable optional components are solid, water soluble or water dispersible organic processing aids of a waxy nature having a Mpt in the range 30°–80° C. The most preferred processing aids have a softening point greater than about 40° C. and a melting point less than about 80° C. to permit their easy processing.

The preferred processing aids serve as plasticisers or thickeners in the incorporation of the precursors into or onto the substrate and ideally are non-hygroscopic solids that are mixed with the precursors and melted to provide mixtures having a viscosity of up to about 30,000 centipoises at 50° C.

Typical solids are $C_{14}$–$C_{18}$ primary and secondary alcohols and $C_{12}$–$C_{20}$ fatty acids and ethoxylates thereof containing from 15 to 80 ethylene oxide groups per mole of alcohol, sorbitan esters of $C_{12}$–$C_{20}$ fatty acids and polyethylene glycols of Mwt 4,000–10,000. As stated hereinbefore, preferred materials are those of low hygroscopicity, particularly the $C_{14}$–$C_{18}$ saturated fatty acids.

The $C_{16}$–$C_{18}$ fatty acids and polyethylene glycols of Mwt 4,000–8,000, are particularly effective when used in amounts such that the weight ratio of compounds:processing aid lies in the range from about 20:1 to about 1:2 particularly from about 4:1 to about 1:1.

In addition to the foregoing optional components that are of primary value in incorporating the precursor onto, and releasing it from, the substrate, conventional detergent ingredients can be incorporated into the composition provided that they are not reactive towards compounds as hereinbefore defined. Thus, surfactants, suds modifiers, chelating agents, anti-redeposition and soil suspending agents, optical brighteners, bactericides, anti-tarnish agents, enzymatic materials, fabric softeners, antistatic agents, perfumes and bleach catalysts can all be introduced into a wash liquor by means of the additive products of the present invention, subject to the constraints imposed by the loading limitations of the substrate.

In detergent additive products in which the compositions comprise a peroxy bleach precursor compound as hereinbefore defined disposed on a substrate of either particulate or non particulate form, the substrate is preferably absorbent and the composition is impregnated therein.

Application of the precursor can be carried out in any convenient manner, and many methods are known in the art. As the preferred acyloxybenzene sulphonate or carboxylate precursors are solid at temperatures in excess of about 150° C., one form of application is by solution in organic solvents which are volatilised after application, whilst another employs a slurry or suspension of the finely divided solid in water or other liquid media.

Preferred compositions in accordance with the invention are substantially anhydrous and thus incorporation on the substrate is best accomplished by utilisation of a non aqueous liquid medium.

A highly preferred embodiment of the invention utilises a processing aid and/or other optional ingredients in molten form as the liquid medium in which the finely divided precursor is dispersed.

Where the substrate comprises a non-sheet like reticulated foam article, direct impregnation of the article by a liquid medium incorporating the dispersed precursor, either alone or with other components of the formulation can be used, employing methods known in the art and described in more detail hereinafter. Where the substrate comprises a non-woven material or a foam article of sheet-like form, it is preferred to mix the bleach precursor with a compatible non-hygroscopic material of melting point ≦about 80° C., such as the processing aids hereinbefore described to provide a waxy solid in which the bleach precursor is present in the form of a solid solution and/or as a dispersed phase. The melting point range and waxy nature of polyethylene glycols of molecular weight ≧about 4000 make them useful for this purpose.

Where nonionic surfactants form components of the composition, their physical properties may permit their use as, or as part of, a liquid medium in which the precursor and other solid components are incorporated.

As previously indicated, materials reactive towards the peroxy bleach precursor compounds of the invention can be incorporated in detergent additive products containing them provided that the precursor and the reactive material are spatially separated from one another. Inorganic peroxygen bleaches which either contain water or hydrogen peroxide in hydrogen bonded form, such as sodium perborate, monohydrate and tetrahydrate, sodium percarbonate, sodium persilicate or sodium perpyrophosphate, and also urea-hydrogen peroxide addition products, are materials which are sufficiently reactive to require this spatial separation.

Where the precursor and the inorganic peroxygen bleach are incorporated in physically separate locations on the same non particulate sheet substrate, a convenient method of application is the deposition of the respective melts, suspensions or solutions as discrete bands of material on the substrate. This can be achieved using a divided extrusion head or by applying the melt or suspension to separate webs of substrate which are subsequently joined longitudinally. Preferably the bleach is applied as a dispersion of solid particles in a molten processing aid (as hereinbefore described) at a temperature in the range from about 40° to about 60° C. Using this technique, bleach:substrate weight ratios of up to about 15:1 can be obtained. This level of loading is attainable with cellular substrates but substrates of fibrous character tend to be limited in practice to bleach:substrate weight ratios of no more than about 8:1. Furthermore, loading limitations imposed by the substrate surface area required for the incorporation of the presursor may limit the amount of bleach to less than than this and bleach:substrate weight ratios in the range from about 5:1 to about 1:2 are normally employed. Provision must also be made for the separation of the bands or areas of bleach and the corresponding bands or areas of precursor during transport and/or storage. This is achieved by interposing layers of material between the layers of substrate or by producing patterns of deposited material that are not coincident on stacking of the substrate.

A preferred method of making the particulate substrate forms of detergent additive product is by applying a spray of the composition as a solution dispersion or molten suspension on to a moving bed of particulate substrate in a rotating drum or pan fluidised bed, or a rotating blade mixer of the Schugi or Patterson-Kelly type.

In a preferred method of making sheet substrate additive products in accordance with the invention, the precursor(s) dissolved or dispersed in a molten processing aid are held in a trough formed by the nip of two horizontal rolls arranged side by side and rotating in opposite directions such that the nip is formed by surfaces having approximately the same velocity in a downward direction. Molten material is spread on one of the rolls and transferred to a continuous web of substrate whose speed is the same as that of the roll and which contacts the roll over a limited length of its periphery. The impregnated substrate is then contacted by a smoothing and spreading roll having a direction of rotation such that its contact surface is moving in the opposite direction to that of the substrate. The rolls employed in this technique are fabricated in metal and are heated to maintain the impregnating mixture in the liquid phase.

A further aspect of the present invention comprises a bleaching composition composed of a precursor compound as hereinbefore defined in combination with a source of hydrogen peroxide in the form of an alkali metal inorganic peroxy salt or a hydrogen peroxide clathrate or composed of the peroxy acid derived from the precursor compound in combination with a stabilising agent.

In the embodiment comprising a mixture of the precursor and a source of alkaline hydrogen peroxide it is very desirable that the two components be isolated from each other in order that a reaction does not occur prior to use. Although a reaction can be prevented by making an anhydrous mixture of the two components, the maintenance of such a mixture in the anhydrous state is very difficult under normal storage conditions. A preferable technique is to separate the components physically, by coating one or both with inert materials that dissolve or disperse in aqueous media, by incorporating each in separate or compartmental packaging, or by fixing each component to separate locations on a non particulate substrate. Each of these separation techniques is well known in the art and does not form part of the present invention.

Bleaching compositions of this type contain from about 30% to about 95% by weight of the hydrogen peroxide source and from about 70% to about 5% by weight of the precursor compound as hereinbefore defined; more generally from about 50% to about 90% of hydrogen peroxide source and from 50% to 10% of precursor compound, most preferably from about 75% to about 90% of hydrogen peroxide source and from about 25% to about 10% of precursor compound.

Where the peroxy acid derived from the precursor compound is employed in the bleaching composition, it can be used in conjunction with a stabilising agent such as quinoline, quinaldic acid, picolinic acid or dipicolinic acid or a derivative thereof, preferably together with a polyphosphate salt. Stabilising agents of this type are disclosed in Sprout U.S. Pat. No. 2,838,459, Sennewald et al U.S. Pat. No. 3,442,937, and Cann U.S. Pat. No. 3,192,255, hereby specifically incorporated herein by reference. A preferred system employs a mixture of 8-hydroxy quinoline and an acid pyrophosphate salt in a ratio of from about 1:1 to about 5:1. The stabilising agents are incorporated at a level of from about 0.005% to about 1.0% by weight of the composition.

In addition, exotherm control agents are also preferred components of solid bleaching compositions incorporating organic peroxy acids, preferred examles of such agents including boric acid as disclosed in Hutchins et al. U.S. Pat. No. 4,100,195, or hydrated inorganic salts as disclosed in Neilsen U.S. Pat. No. 3,770,816, both patents being hereby specifically disclosed herein by reference.

The present invention also embraces the formation of aqueous bleaching liquors by means of the reaction of a source of alkaline hydrogen peroxide with additive products containing precursors of an aliphatic peroxy acid whose carboxylic acid analogue has a log $P_{OCT}$ of from about 1.9 to about 4.1 particularly with the $C_6$–$C_{16}$ branched alkyl group-containing precursor compounds specifically described above, or by means of the addition of the above-described detergent or bleaching compositions to an aqueous medium. Aqueous bleaching liquors in accordance with this aspect of the invention develop low intensity or bland odours which are compatible with and/or capable of being masked by the perfume compositions conventionally used in detergent products. Aqueous bleaching liquors containing the most highly preferred compounds in accordance with the invention are virtually odourless whereas the analogous linear alkyl chain materials have a pungent odour which is aesthetically undesirable.

In addition to the non linear precursor compounds of the present invention, products and compositions made in accordance with the invention may optionally contain any of the organic peroxy acid bleach precursors known in the art. A detailed disclosure of such precursors is provided in British Patent Specification No. 2040983, said disclosure being hereby specifically incorporated herein by reference. For the purposes of the present invention, blends of branched $C_8$–$C_{10}$ acyl oxybenzene sulphonate or carboxylate with peracetic acid precursors are preferred, examples of such peracetic acid precursors including tetra acetyl ethylene diamine, tetra acetyl methylene diamine, tetra acetyl glycouril, sodium p-acetoxybenzene sulphonate, penta acetyl glucose, octa acetyl lactose. However, the invention also contemplates blends of branched $C_8$–$C_{10}$ carbon chain-containing precursors with e.g. peroxybenzoic and peroxyphthalic acid precursors where different combinations of bleaching properties are required.

In blends of the preferred branched $C_8$–$C_{10}$ acyl oxybenzene sulphonate precursors with other peroxyacid precursors it has been found that the $C_8$–$C_{10}$ acyl oxybenzene sulphonate should preferably be present in an amount to provide a level of at least about 2 ppm and preferably at least about 5 ppm available oxygen in the wash liquor, in order that the benefit of the $C_8$–$C_{10}$ peroxy acid can be realised. Generally the weight ratio of the $C_8$–$C_{10}$ acyl oxybenzene sulphonate precursor to the other peroxy acid (e.g. peracetic acid) precursor should be such as to provide a $C_8$–$C_{10}$ aliphatic peroxy acid:peracetic acid molar ratio in the range from about 3:1 to about 1:5 preferably from about 2:1 to about 1:3 most preferably from about 1.8:1 to about 1:2. Under European washing conditions, blends in which the $C_8$–$C_{10}$ acyl oxybenzene sulphonate delivers from 5–15 ppm available oxygen in the wash liquor are preferred.

The level of usage of the precursor will naturally be dependent on a number of factors e.g. the size of the fabric load in the machine, the level of bleaching performance desired, the amount of perhydroxyl ion in the wash solution, the bleaching efficacy of the organic peroxy species derived from the precursor and the efficiency of conversion of the precursor into that peroxy species. It is conventional with inorganic peroxy bleaches to provide a level of available oxygen in solution from about 50 ppm to about 350 ppm by weight for heavy duty laundry purposes. However, when using organic peroxy bleaches a level of available oxygen provided by the organic peroxy compound may lie in the range from about 1 ppm to about 50 ppm, levels of from about 1.5 ppm to about 16 ppm being appropriate under conventional US washing conditions while levels of from about 20 pm to about 50 ppm are more commonly used under European washing conditions. This level of available oxygen should be attained within the normal wash cycle time i.e. within 5–25 minutes depending on the particular wash cycle being employed.

For a machine having a liquid capacity in use of 20 to 30 liters, such a level of available oxygen requires the delivery of from about 1 gr to about 20 gr of organic peroxy compound percursor assuming quantitative conversion.

Various aspects of the invention are illustrated in the following Examples in which all parts and percentages are by weight unless otherwise specified.

$C_{12}$ LAS: Sodium linear $C_{12}$ alkyl benzene sulphonate
$C_{13}$ LAS: Sodium linear $C_{13}$ alkyl benzene sulphonate
ASC: Disodium salt of -sulphonated stearic acid
TAS: Sodium tallow alcohol sulphate
$C_{14/15}$ AS: Sodium $C_{14}$–$C_{15}$ alkyl sulphate
$C_{12/14}$ AS: Sodium $C_{12}$–$C_{14}$ alkyl sulphate
$TAE_n$: Tallow alcohol ethoxylated with n moles of ethylene oxide per mole of alcohol
$C_{14}$TMAB: $C_{14}$ alkyl trimethyl ammonium bromide
$C_{14}$ TMAMS: $C_{14}$ alkyl trimethyl ammonium methyl sulphate
$C_{12}$TMAB: $C_{12}$ alkyl trimethyl ammonium bromide
A 45E7: A $C_{14-15}$ primary alcohol condensed with 7 moles of ethylene oxide.
A 23 E6.5: A $C_{12}$–$C_{13}$ primary alcohol condensed with 6.5 moles of ethylene oxide.
Soap: Sodium salt of 80/20 mixture of tallow and coconut fatty acids.
PEG: Polyethylene glycol (MWt normally follows)
TAED: Tetraacetyl ethylene diamine
PAG: Penta acetyl glucose
AOBS: Sodium p-acetoxy benzene sulphonate
ISONOBS: Sodium 3,5,5 trimethyl hexanoyl oxybenzene sulphonate
ISONOBA: Sodium 3,5,5 trimethyl hexanoyl oxybenzoic acid
EHOBS: Sodium 2-ethyl hexanoyl oxybenzene sulphonate
Silicate: Sodium silicate having an $SiO_2$:$Na_2O$ ratio of 1.6
Sulphate: Anhydrous sodium sulphate
STP: Sodium tripolyphosphate
Zeolite A: Sodium aluminosilicate of formula $Na_{12}$.$(ALO_2.SiO_2)_{12}27H_2O$.
Carbonate: Anhydrous sodium carbonate
CMC: Sodium carboxymethyl cellulose
Silicone Compound: 85% polydimethyl siloxane 15% silica
Silicone Prill: Comprising 0.14 parts by weight of an 85:15 by weight mixture of silanated silica and silicone, granulated with 1.3 parts of sodium tripolyphosphate, and 0.56 parts of tallow alcohol condensed with 80 molar proportions of ethylene oxide
MA/AA: Copolymer of 1:4 maleic/acrylic acid, average molecular weight about 80,000.
MVEMA Maleic anhydride/vinyl methyl ether copolymer, believed to have an average molecular weight of 240,000. This material was prehydrolysed with NaOH before addition.
Perborate: Sodium perborate tetrahydrate of nominal formula $NaBO_2.3H_2O.H_2O_2$
Perborate monohydrate: Anhydrous sodium perborate bleach of empirical formula $NaBO_2.H_2O_2$
Enzyme: Mixed proteolytic and and amylolytic enzyme sold by Novo Industrie AS.
EDTA: Sodium ethylene diamine tetra acetate
NTA: Sodium nitrilotriacetate.
Brightener 1: Disodium 4,4'-bis(2-morpholino-4-anilino-s-tgriazin-6-ylamino)stilbene-2:2'-disulphonate.

Brightener 2: Disodium 4,4'-bis(2-sulphonato styryl)-biphenyl
DETPMP: Diethylene triamine penta(methylene phosphonic acid), marketed by Monsanto under the Trade name Dequest 2060
EDTMP: Ethylenediamine tetra (methylene phosphonic acid), marketed by Monsanto, under the Trade name Dequest 2041
$H_2O_2$ Clathrate: A clathrate of $4Na_2SO_4:2H_2O_2:1NaCl$
Mixed Suds Suppressor: 25% paraffin wax Mpt 501C, 17% hydrophobic silica, 58% paraffin oil.

EXAMPLE 1

Preparation of sodium 3,5,5 trimethyl hexanoyl oxybenzene sulphonate 100 gms of dehydrated sodium phenol sulphonate and 117 gms (30% molar excess) of isononanoyl chloride* (ex Akzo BV, Mwt 176.5) were weighed into a 2 liter conical flask. The flask was fitted with magnetic stirrer and carried a 2-way head fitted with an Airflux condenser and a nitrogen inlet tube leading to the base of the flask. 500 mls chlorobenzene were added and the resulting suspension was stirred. 5 gms of tetrabutylammonium bromide (supplied by Aldrich Chemical Co. Inc., Milwaukee, Wisc. 53233, USA) were added as catalyst and the resulting suspension was stirred and heated to 120° C. with nitrogen passing through the flask. Heating was continued with nitrogen passing, for 19.5 hours.
*This is the common term used in the trade to describe 3,5,5 trimethyl hexanoyl chloride.

The reaction mixture was then cooled to room temperature, poured into 3 liters of diethyl ether and well washed using a Silverson stirrer. The solid material was filtered off by Buchner filtration and the resulting solid was washed with 2×2 liters of ether, filtering off after each wash. The resulting solid was dried over $P_2O_5$ in a vacuum desiccator, was powdered in a coffee grinder and re-dried in a vacuum desiccator over $P_2O_5$. The yield was 140 gms and NMR analysis showed the solid to comprise 92% sodium 3,5,5 trimethyl hexanoyl oxybenzene sulphonate and 8% sodium phenol sulphonate.

EXAMPLE 2

Preparation of sodium 3,5,5 trimethyl hexanoyl oxybenzoic acid

The same apparatus was used as in Example 1. 74.5 g of p-hydroxybenzoic acid was mixed with 100 g of 3,5,5-trimethyl hexanoyl chloride (5% molar excess) and 3.7 g of tetrabutyl ammonium bromide catalyst. The mixture was stirred and heated to 100° C. in a current of nitrogen for 2 hours. The resultant white, porous, solid mass was cooled, broken up under petroleum ether (bp 40°-60° C.), filtered, washed and dried. The product, 126 g (84%) was found by NMR analysis to be 95% 3,5,5 trimethyl hexanoyl oxybenzoic acid and 5% p-hydroxy benzoic acid.

EXAMPLES 3-8

Detergent compositions incorporating a compound in accordance with Example 1 have the following percentage formulations:

|  | 3 | 4 | 5 | 6 | 7 | 8 |
|---|---|---|---|---|---|---|
| $C_{12}$ LAS | — | 6.0 | 4.7 | — | — | 6.0 |
| $C_{13}$ LAS | 4.0 | — | — | 9.0 | 8.0 | — |
| $C_{14/15}$ AS | 8.0 | 6.0 | 7.0 | 3.0 | — | 6.0 |

-continued

|  | 3 | 4 | 5 | 6 | 7 | 8 |
|---|---|---|---|---|---|---|
| A45E7 | — | 2.0 | 2.1 | 2.5 | — | 2.0 |
| $C_{14}$ TMAB | 2.0 | 2.0 | 2.1 | — | 1.5 | 2.0 |
| $C_{12}$ TMAB | — | — | — | 1.5 | — | — |
| STP | 24.0 | 24.0 | 18.0 | 32.0 | 24.0 | 12.0 |
| MA/AA | 1.5 | 1.7 | — | — | 1.5 | 3.0 |
| MVEMA | — | — | 1.0 | 0.5 | 0.5 | — |
| Silicate | 10.0 | 5.0 | 7.5 | 5.0 | 7.5 | 5.0 |
| Carbonate | 5.0 | 10.0 | 5.0 | — | 2.5 | 10.0 |
| EDTMP | 0.25 | 0.3 | 0.1 | 0.1 | 0.1 | 0.2 |
| Perborate | 18.0 | 21.0 | 24.0 | 24.0 | 18.0 | 21.0 |
| Peroxy acid precursor | 3.0 | 3.0 | 5.0 | 3.0 | 3.0 | 8.5 |
| Silicone Prill | 3.0 | 4.0 | 4.0 | 2.5 | 2.0 | 4.0 |
| Brightener 1 | 0.25 | 0.25 | 0.20 | 0.25 | 0.25 | 0.20 |
| Enzyme | 0.4 | 0.3 | 0.4 | 0.25 | 0.30 | 0.30 |
| Sulphate | 9.0 | 5.0 | 12.0 | 6.4 | 15.35 | 15.0 |
| Moisture + Misc. | To 100 | | | | | |

Typically a spray dried base powder is made containing the anionic and cationic surfactants, STP, inorganic salts, brightener, copolymer and EDTMP and then the remaining ingredients are incorporated by spray on to the base powder nonionic, dry mixing (perborate) or via prill addition (peroxy acid precursor, silicone and enzyme).

An additional comparative formulation 4A was made up in accordance with Example 4 except that the peroxy acid precursor had the structural formula

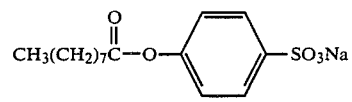

Formulations 4 and 4A were each made up into a 0.2% by weight aqueous solution at 60° C., and both formulations displayed a rate of perhydrolysis that was 95% complete after 2 minutes. However, whilst formulation 4A had a strong bleachy odor, formulation 4 was virtually odorless. Application of perfume by spray on to both formulations prior to making up the aqueous solutions did not mask the solution odor of formulation 4A, whilst providing the expected pleasant odor to the solution of formulation 4.

EXAMPLES 9-14

The following formulations represent examples of the detergent composition aspect of the invention.

|  | 9 | 10 | 11 | 12 | 13 | 14 |
|---|---|---|---|---|---|---|
| LAS | 4 | 8 | 8 | — | 7 | 5 |
| $C_{14/15}$ AS | 4 | — | — | 9 | — | 3 |
| TAS | — | — | 4 | 3 | — | — |
| $C_{12/14}$ AS | — | — | — | — | 2 | — |
| $C_{12}$ TMAB | — | 2 | 2 | — | 2 | — |
| Dobanol 45-E-7 | 4 | 6 | 5 | 6 | 5 | 10 |
| $TAE_{11}$ | — | 0.5 | — | — | 2 | — |
| TAED | 0.5 | — | 6 | — | — | — |
| Silicate | 5 | 6 | 3 | 7 | 4 | 10 |
| Mixed Suds Suppressor | 2 | — | — | 2 | — | 2 |
| Silicone Prill | — | — | 2 | 3 | — | 0.5 |
| MVEMA | — | — | 0.8 | 1.5 | — | 1 |
| MA/AA | 2 | 1 | — | — | 1.2 | — |
| Brightener 1 | 0.3 | 0.2 | 0.4 | 0.3 | 0.2 | 0.2 |
| DETPMP | 0.3 | — | — | — | — | 0.2 |
| EDTMP | — | — | 0.4 | — | — | — |
| Sodium Perborate | 12 | 15 | 16 | 18 | 10 | 15 |
| Enzyme | 0.6 | 1 | — | — | — | 0.8 |
| Sodium Tripolyphosphate | 30 | 28 | 25 | 32 | 28 | 30 |
| Magnesium Sulphate | — | 0.5 | — | — | — | 0.5 |

-continued

|  | 9 | 10 | 11 | 12 | 13 | 14 |
|---|---|---|---|---|---|---|
| ISONOBS | 2.5 | 4 | — | — | 3 | — |
| EHOBS | — | — | 2 | — | — | 5 |
| ISONOBA | — | — | 1.5 | 6 | — | — |
| Sodium Sulphate, Moisture and Miscellaneous | | | To 100 | | | |

EXAMPLES 15–20

Laundry additive products incorporating precursor compounds in water releasable combination with a sheet substrate are prepared having the compositions shown below in parts by weight.

|  | 15 | 16 | 17 | 18 | 19 | 20 |
|---|---|---|---|---|---|---|
| ISONOBS | 7.6 | 5.2 | 10.5 | 8.4 | 4.2 | 5.2 |
| PAG | — | — | — | 2.5 | 4.0 | — |
| TAED | — | 3.6 | — | — | — | — |
| AOBS | — | — | — | — | — | 3.0 |
| A45E7 | 5.0 | 5.0 | 5.0 | 5.0 | 5.0 | 5.0 |
| PEG 8000 | 5.0 | 7.0 | 8.0 | 8.0 | 6.0 | 6.0 |
| C$_{14}$TMAB | — | 2.0 | — | — | 2.0 | — |
| C$_{14}$TMAMS | — | — | — | 2.0 | — | 2.0 |
| EDTMP | 0.5 | 0.5 | 0.5 | 0.5 | 0.5 | 0.5 |
| MVEMA | 0.3 | 0.3 | 0.3 | 0.3 | 0.3 | 0.3 |
| Silicone Compound | 0.25 | 0.25 | 0.25 | 0.25 | 0.25 | 0.25 |
| Brightener 2 | 0.1 | 0.1 | 0.1 | 0.1 | 0.1 | 0.1 |
| Perfume | 0.1 | 0.1 | 0.1 | 0.1 | 0.1 | 0.1 |
| Substrate | 2.8 | 2.8 | 2.8 | 2.8 | 2.8 | 2.8 |

The substrate in each instance is a square patterned apertured non-woven sheet, of size 23×35 cm and basis weight 2.8 g, formed of 100% unbleached crimped rayon fibres (80% fibre, 20% polyacrylate binder). In the case of Examples 15 and 17 the products are made by forming a melt of the PEG and A 45E7 at approximately 80° C., dispersing the other components (except the perfume) therein and applying the resultant slurry to the substrate from an applicator roll with which the substrate is brought into contact. Additional rolls are used to spread the slurry before it is cooled to ambient temperature to solidify the composition. Perfume is then sprayed on to the impregnated substrate to produce the final product.

Examples 16 and 18–20 use a similar procedure except that the product is applied to the sheet via a divided extruder head instead of an applicator roll, the division permitting the cationic surfactant, together with 1.0 part of A45E7 and 2.0 parts of PEG 8000 from the formulation to be applied as a separate stripe.

EXAMPLE 21

A bleaching composition in the form of the aliphatic peroxy acid derivative of the compound of Example 1 comprises:

| 3,5,5-trimethyl peroxyhexanoic acid | 18.2% |
|---|---|
| Boric acid | 67.8% |
| 8-hydroxyquinoline | 0.05% |
| Disodium dihydrogen pyrophosphate | 0.05% |
| Minors, including 10% sodium sulphate | 13.9% |
|  | 100.00 |

EXAMPLES 22–26

The following formulations are further detergent compositions in accordance with the invention.

|  | 22 | 23 | 24 | 25 | 26 |
|---|---|---|---|---|---|
| LAS | 4 | 8 | — | 7 | — |
| C$_{14/15}$ AS | 4 | — | — | — | — |
| TAS | — | 4 | — | 2 | — |
| ASC | — | — | 15 | — | 20 |
| Soap | — | 2 | 10 | — | 25 |
| Dobanol 45-E-7 | 4 | 5 | 6 | 5 | 10 |
| TAED | 1 | 1 | — | 1 | — |
| Silicate | 5 | 3 | 7 | 4 | 10 |
| Mixed Suds Suppressor | 2 | — | — | — | .2 |
| Silicone Prill | — | 2 | 3 | — | 0.5 |
| MVEMA | — | 0.8 | 1.5 | — | 1 |
| NTA | — | 2.5 | — | 2.5 | 5 |
| Brightener 1 | 0.3 | 0.4 | 0.3 | 0.2 | 0.2 |
| DETPMP | — | — | — | — | 0.2 |
| EDTMP | 1 | — | — | 1 | — |
| Sodium Perborate | 12 | 16 | 18 | 10 | 15 |
| Enzyme | 0.6 | — | — | — | 0.8 |
| Zeolite A | 30 | 25 | — | 10 | — |
| Carbonate | 10 | 5 | 15 | 20 | — |
| Sodium citrate | — | — | 10 | — | 5 |
| ISONOBS | 3 | 4 | — | 3 | — |
| EHOBS | — | — | — | — | 5 |
| ISONOBA | — | — | 6 | — | — |
| Sodium Sulphate, Moisture and Miscellaneous | | | To 100 | | |

What we claim is:

1. A non-linear aliphatic peroxycarboxylic acid precursor adapted to form a non linear aliphatic peroxy acid in aqueous alkaline hydrogen peroxide solution wherein the precursor has the general formula:

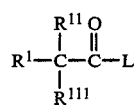

wherein the group:

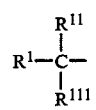

is an organic moiety of non linear structural configuration R$^{II}$ and R$^{III}$ being independently selected from the group consisting of hydrogen and C$_1$–C$_4$ alkyl groups, the group:

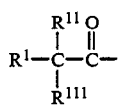

being the acyl moiety of a carboxylic acid having a log P$_{oct}$ of from about 1.9 to about 4.1, wherein P$_{oct}$ is the partition coefficient of the carboxylic acid between n-octanol and water at 21° C., and L is a leaving group selected from the group consisting of

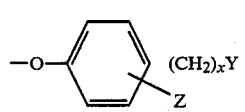

(a)

-continued

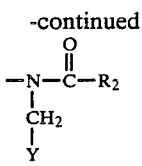
(b)

wherein Z is selected from the group consisting of H, $R_2$ and halide, $R_2$ is an alkyl group containing from 1 to 4 carbon atoms, x is 0 or an integer from 1 to 4 and Y is selected from the group consisting of —$SO_3M$
—$OSO_3M$
—$CO_2M$
—$N^+(R_2)_3Q^-$
—$N(R_2)_2 \to O$ wherein M is selected from the group consisting of H, alkali metal, alkali earth meal, ammonium and substituted ammonium and Q is a halide or methosulphate.

2. A non-linear aliphatic peroxycarboxylic acid precursor according to claim 1 wherein $R^I$ is a hydrocarbyl moiety.

3. A non-linear aliphatic peroxycarboxylic acid precursor according to claim 1 wherein the conjugate acid of leaving group L has a pKa in the range from about 7 to about 11.

4. A non-linear aliphatic peroxycarboxylic acid precursor according to claim 2 wherein $R^I$ is a group of formula

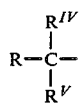

wherein $R^{IV}$ and $R^V$ are each independently selected from the group consisting of hydrogen and $C_1$–$C_4$ alkyl groups, and the group:

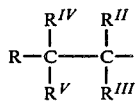

is a $C_6$–$C_{16}$ alkyl group in which at least one of $R^{II}$, $R^{III}$, $R^{IV}$ and $R^V$ is $C_1$–$C_4$ alkyl, there being a linear alkyl chain of at least five carbon atoms extending from and including the carbonyl carbon.

5. A non linear aliphatic peroxycarboxylic acid precursor according to claim 1 wherein:

is a $C_6$–$C_{12}$ group wherein $R^{II}$ and $R^{III}$ are hydrogen atoms.

6. A non-linear aliphatic peroxycarboxylic acid precursor according to claim 5 wherein:

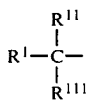

is a $C_7$–$C_9$ group.

7. A non-linear aliphatic peroxycarboxylic acid precursor according to claim 6 wherein $R^I$ has the formula

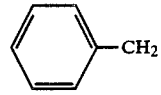

8. A compound according to claim 6 wherein L has the formula (a) in which Z is H, x is 0 and Y is selected from —$SO_3M$ and —$CO_2M$, the conjugate acid of L having a pKa in the range from about 8 to about 10.

9. An alkali metal ammonium or tri $C_2$–$C_3$ alkanolammonium 2-ethyl hexanoyl oxybenzene sulphonate.

10. An alkali metal ammonium or tri $C_2$–$C_3$ alkanolammonium 3,5,5,trimethyl hexanoyl oxybenzene sulphonate.

11. 2-ethyl hexanoyl oxybenzoic acid and alkali metal, alkaline earth metal, ammonium and tri $C_2$–$C_3$ alkanolammonium salts thereof.

12. 3,5,5,trimethyl hexanoyl oxybenzoic acid and alkali metal, alkaline earth metal, ammonium and tri $C_2$–$C_3$ alkanol ammonium salts thereof.

13. A solid detergent composition comprising an organic surfactant, a source of alkaline hydrogen peroxide and a non-linear aliphatic peroxycarboxylic acid precursor wherein the precursor has the general formula

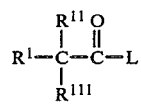

wherein the group:

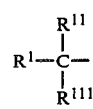

is an organic moiety of non linear structural configuration, $R^{II}$ and $R^{III}$ being independently selected from the group consisting of hydrogen and $C_1$–$C_4$ alkyl groups, the group:

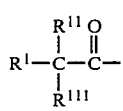

being the acyl moiety of a carboxylic acid having a log $P_{oct}$ of from about 1.9 to about 4.1, wherein $P_{oct}$ is the partition coefficient of the carboxylic acid between n-octanol and water at 21° C., and L is a leaving group selected from the group consisting of

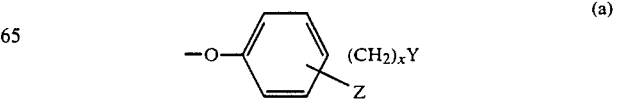
(a)

$$-N-\overset{\overset{O}{\|}}{C}-R_2 \quad (b)$$
$$\underset{Y}{\overset{|}{CH_2}}$$

wherein Z is selected from the group consisting of H, R$_2$ and halide, R$_2$ is an alkyl group consisting from 1 to 4 carbon atoms, x is 0 or an integer from 1 to 4 and Y is selected from the group consisting of

—SO$_3$M
—OSO$_3$M
—CO$_2$M
—N$^+$(R$_2$)$_3$Q$^-$
—N(R$_2$)$_2$→O wherein M is selected from the group consisting of H, alkali metal, alkali earth metal, ammonium or substituted ammonium and Q is a halide or methosulphate.

14. A solid detergent composition according to claim 13 wherein the group R$^I$ of said precursor is a hydrocarbyl moiety.

15. A solid detergent composition according to claim 14 wherein the organic surfactant is selected from the group consisting of anionic, nonionic and cationic surfactants and mixtures thereof and the source of hydrogen peroxide comprises an alkali metal perborate or precarbonate or a hydrogen peroxide clathrate, the molar ratio of said alkaline hydrogen peroxide to the precursor being at least about 1.5:1.

16. A solid detergent composition according to claim 15 wherein the group $$R^1-\overset{\overset{R^{11}}{|}}{\underset{\underset{R^{111}}{|}}{C}}-$$

is a C$_7$–C$_9$ group.

17. A solid detergent composition according to claim 16 wherein L has the formula (a) in which Z is H, x is 0 and Y is selected from —SO$_3$M and —CO$_2$M.

18. A solid detergent composition according to claim 16 incorporating a peroxy acetic acid precursor selected from the group consisting of tetracetyl ethylene diamine, tetracetyl methylene diamine, sodium p-acetoxybenzene sulphonate, tetracetyl glycouril, penta acetyl glucose and octa acetyl lactose and mixtures thereof, the amounts of said non-linear aliphatic peroxy acid precursor and peroxyacetic acid precursor being such as to provide a non-linear aliphatic peroxy acid:peracetic acid molar ratio in the range from about 3:1 to about 1:5.

19. A solid detergent composition according to claim 18 wherein the amounts of non-linear peroxyacid precursor and peracetic acid precursor are such as to give a non-linear aliphatic peroxy acid:peracetic acid molar ratio of from about 2:1 to about 1:3.

20. A laundry additive product adapted for addition to an aqueous laundry liquor containing a source of alkaline hydrogen peroxide, said product incorporating a non-linear aliphatic peroxy carboxylic acid precursor having the general formula $$R^1-\overset{\overset{R^{11}}{|}}{\underset{\underset{R^{111}}{|}}{C}}-\overset{\overset{O}{\|}}{C}-L$$

wherein the group:

$$R^1-\overset{\overset{R^{11}}{|}}{\underset{\underset{R^{111}}{|}}{C}}-$$

is an organic moiety of non linear structural configuration, R$^{II}$ and R$^{III}$ being independently selected from the group consisting of hydrogen and C$_1$–C$_4$ alkyl groups, the group:

$$R^1-\overset{\overset{R^{11}}{|}}{\underset{\underset{R^{111}}{|}}{C}}-\overset{\overset{O}{\|}}{C}-$$

being the acyl moiety of a carboxylic acid having a log P$_{oct}$ of from about 1.9 to about 4.1, wherein P$_{oct}$ is the partition coefficient of the carboxylic acid between n-octanol and water at 21° C., and L is a leaving group selected from the group consisting of $$-O-\underset{Z}{\underset{|}{\bigcirc}}-(CH_2)_xY \quad (a)$$

$$-N-\overset{\overset{O}{\|}}{C}-R_2 \quad (b)$$
$$\underset{Y}{\overset{|}{CH_2}}$$

wherein Z is selected from the group consisting of H, R$_2$ and halide, R$_2$ is an alkyl group consisting from 1 to 4 carbon atoms, x is 0 or an integer from 1 to 4 and Y is selected from the group consisting of

—SO$_3$M
—OSO$_3$M
—CO$_2$M
—N$^+$(R$_2$)$_3$Q$^-$
—N(R$_2$)$_2$→O wherein M is selected from the group consisting of H, alkali metal, alkali earth metal, ammonium or substituted ammonium and Q is a halide or methosulphate; said product being enclosed within a container which allows access of water to the interior thereof on immersion in the liquor.

21. A laundry additive product according to claim 20 wherein the container is water impermeable and is provided with a water frangible closure.

22. A laundry additive product according to claim 21 wherein the container comprises a flexible pouch or bag made of synthetic polymeric film material.

23. A laundry additive product according to claim 21 wherein the water frangible closure comprises a water soluble adhesive.

24. A laundry additive product adapted for addition to an aqueous laundry liquor containing a source of alkaline hydrogen peroxide, said product incorporating a non-linear aliphatic peroxycarboxylic acid precursor having the general formula

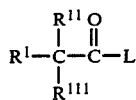

wherein the group:

is an organic moiety of non linear structural configuration, $R^{II}$ and $R^{III}$ being independently selected from the group consisting of hydrogen and $C_1$–$C_4$ alkyl groups, the group:

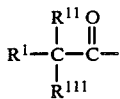

being the acyl moiety of a carboxylic acid having a log $P_{oct}$ of from about 1.9 to about 4.1, wherein $P_{oct}$ is the partition coefficient of the carboxylic acid between n-octanol and water at 21° C., and L is a leaving group selected from the group consisting of

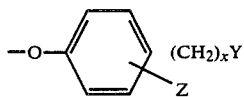 (a)

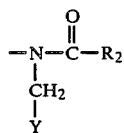 (b)

wherein Z is selected from the group consisting of H, $R_2$ and halide, $R_2$ is an alkyl group containing from 1 to 4 carbon atoms, x is 0 or an integer from 1 to 4 and Y is selected from the group consisting of
—$SO_3M$
—$OSO_3M$
—$CO_2M$
—$N^+(R_2)_3Q^-$
—$N(R_2)_2\rightarrow O$
wherein M is selected from the group consisting of H, alkali metal, alkali earth metal, ammonium or substituted ammonium and Q is a halide or methosulphate; said precursor being in water releasable combination with a non particulate flexible substrate, the weight ratio of said precursor to said substrate being in the range of from about 1:10 to about 30:1.

25. A laundry addtive product according to claim 24 wherein the group $R^I$ of said precursor is a hydrocarbyl moiety.

26. A laundry additive product according to claim 25 wherein the group

is a $C_7$–$C_9$ group.

27. A laundry additive product according to claim 26 wherein L has the formula (a) in which Z is H, x is 0 and Y is selected from —$SO_3M$ and —$CO_2M$.

28. A laundry additive product according to claim 27 wherein the precursor is an alkali metal 3,5,5 trimethyl hexanoyl oxybenzene sulphonate.

29. A laundry additive product adapted for addition to an aqueous laundry liquor containing a source of alkaline hydrogen peroxide said product consisting essentially of; (a) a composition incorporating an organic peroxyacid bleach precursor of formula

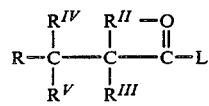

wherein $R^{II}$, $R^{III}$, $R^{IV}$, and $R^V$ are each independently selected from the group consisting of hydrogen and $C_1$–$C_4$ alkyl groups, the group

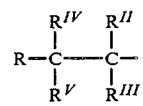

is a $C_6$–$C_{16}$ alkyl group in which at least one of $R^{II}$, $R^{III}$, $R^{IV}$ and $R^V$ is $C_1$–$C_4$ alkyl, there being a linear chain of at least five carbon atoms extending from and including the carbonyl carbon, L is a leaving group of formula

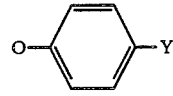

where Y is selected from —$SO_3M$ and —$CO_2M$ where M is selected from H, alkali metal or alkali earth metal, said composition also incorporating one or more detergent components selected from the group consisting of organic surfactants, detergent builder salts, chelating agents and mixtures thereof, (b) a non particulate flexible substrate; said composition being in water releasable combination with said substrate, the weight ratio of said precursor to said substrate being in the range from about 1:10 to about 3:1 and the weight of ratio of said detergent components other than said precursor to said substrate being not greater than about 10:1.

30. A laundry additive product according to claim 29 wherein the composition further includes a peracetic acid precursor selected from the group consisting of tetracetyl ethylene diamine tetracetyl methylene diamine, sodium p-acetoxybenzene sulphonate, tetracetyl glycouril, penta acetyl glucose and octa acetyl lactose and mixtures thereof, the amounts of said non-linear aliphatic acid precursor to the peroxyacetic acid precursor being such as to provide a non-linear aliphatic peroxy acid:peracetic acid molar ratio in the range from about 3:1 to about 1:5.

31. A laundry additive product according to claim 29 wherein the substrate is a laminated sheet.

32. A laundry additive product according to claim 29 wherein said substrate is a non woven fibrous sheet and the weight ratio of said compound to said substrate is in the range from about 1:2 to about 10:1.

33. A laundry additive product according to claim 29 incorporating a source of hydrogen peroxide selected from the group consisting of sodium perborate tetrahydrate, sodium perborate monohydrate, sodium persilicate, sodium perpyrophosphate and urea-hydrogen peroxide addition products, said source of hydrogen peroxide being spatially separated from said precursor compound on said substrate.

34. A bleaching composition consisting essentially of a source of hydrogen peroxide selected from the group consisting of an alkali metal inorganic peroxy salts and hydrogen peroxide clathrates in combination with a non-linear aliphatic peroxy compound precursor of general formula

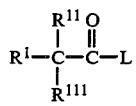

wherein the group:

is an organic moiety of non linear structural configuration, $R^{II}$ and $R^{III}$ being independently selected from the group consisting of hydrogen and $C_1$–$C_4$ alkyl groups, the group:

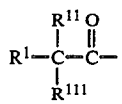

being the acyl moiety of a carboxylic acid having a log $P_{oct}$ of from about 1.9 to about 4.1, wherein $P_{oct}$ is the partition coefficient of the carboxylic acid between n-octanol and water at 21° C., and L is a leaving group selected from the group consisting of

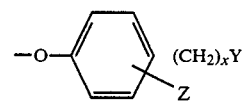

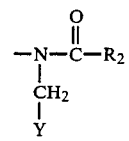

wherein Z is selected from the group consisting of H, $R_2$ and halide, $R_2$ is an alkyl group containing from 1 to 4 carbon atoms, x is 0 or an integer from 1 to 4 and Y is selected from the group consisting of —$SO_3M$
—$OSO_3M$
—$CO_2M$
—$N^+(R_2)_3Q^-$
—$N(R_2)_2 \rightarrow O$ wherein M is selected from the group consisting of H, alkali metal, alkali earth metal, ammonium or substituted ammonium and Q is a halide or methosulphate.

35. A bleaching composition comprising an aliphatic percarboxylic acid of formula R—COOOH wherein R is a $C_6$–$C_{16}$ aliphatic group branched in at least the 2- and/or 3-position with respect to the carbonyl carbon atom, there being a linear alkyl chain of at least 5 carbon atoms extending from and including the carbonyl carbon, in combination with an effective amount of stabilising agent for said aliphatic percarboxylic acid.

36. A method of forming a laundry bleaching liquor having a bland odour comprising the step of adding a non-linear aliphatic peroxy acid precursor in accordance with claim 1 to an aqueous liquor containing a source of alkaline hydrogen peroxide in an amount of from about 50 to about 350 parts per million.

37. A method of forming a laundry bleaching liquor having a bland odour comprising the step of adding a product in accordance with claim 20 to an aqueous liquor containing a source of alkaline hydrogen peroxide in an amount of from about 50 to about 350 parts per million.

38. A method of forming a laundry bleaching liquor having a bland odour comprising the step of adding a product in accordance with claim 24 to an aqueous liquor containing a source of alkaline hydrogen peroxide in an amount of from about 50 to about 350 parts per million.

39. An aqueous alkaline laundry bleaching liquor having a bland odour containing from about 2 to about 15 ppm available oxygen produced by perhydrolysis of a non-linear aliphatic peroxy acid precursor in accordance with claim 1.

* * * * *